US008680151B2

(12) United States Patent
Ruan et al.

(10) Patent No.: US 8,680,151 B2
(45) Date of Patent: Mar. 25, 2014

(54) COMPOUNDS, COMPOSITIONS AND METHODS FOR TREATING OR PREVENTING HYPOXIC OR ISCHEMIC INJURY

(75) Inventors: Fuqiang Ruan, Bellevue, WA (US); Edward A. Wintner, Belmont, MA (US); Thomas L. Deckwerth, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 53 days.

(21) Appl. No.: 13/025,830

(22) Filed: Feb. 11, 2011

(65) Prior Publication Data

US 2011/0195945 A1 Aug. 11, 2011

Related U.S. Application Data

(60) Provisional application No. 61/303,532, filed on Feb. 11, 2010.

(51) Int. Cl.
*A61K 31/16* (2006.01)
*C07C 231/12* (2006.01)

(52) U.S. Cl.
USPC .......................................... 514/616; 564/154

(58) Field of Classification Search
USPC ....................... 514/885, 616; 554/47; 564/154
See application file for complete search history.

(56) References Cited

U.S. PATENT DOCUMENTS 6,288,250 B1 9/2001 Bergstrand et al.
2008/0199541 A1 8/2008 Tomaselli et al.

OTHER PUBLICATIONS

Berge, Stephen M. "Pharmaceutical Salts", *Journal of Pharmaceutical Sciences*, vol. 66, No. 1 Jan. 1977, 1-19.
Distrutti, Eleonora "5-Amino-2hydroxybenxoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity", *JPET*, vol. 319, No. 1 2006, 447-458.
Fiorucci, Stefano "Inhibition of Hydrogen Sulfide Generation Contributes to Gastric Injury Caused by Anti-Inflammatory Nonsteriodal Drugs", *Gastroenterology 129* 2005, 1210-1224.
Fiorucci, Stefano "The Third Gas: $H_2S$ Regulates Perfusion Pressure in Both the Isolated and Perfused Normal Rat Liver and in Cirrhosis", *Hepatology* 2005, 539-548.
Geng, Bin "$H_2S$ generated by heart in rat and its effects on cardiac function", *Biochemical and Biophysical Research Communications 313* 2004, 362-368.
Haynes, Delia A. "Occurrence of Pharmaceutically Acceptable Anions and Cations in the Cambridge Structural Database", *Journal of Pharmaceutical Sciences*, vol. 94, No. 10 Oct. 2005, 2111-2120.
Hui, Yan "Changes in arterial hydrogen sulfide ($H_2S$) content during septic shock and endotoxin shock in rats", *Journal of Infection 47* 2003, 155-160.
Johansen, David "Exogenous hydrogen sulfide ($H_2S$) protects against regional myocardial ischemia-reperfusion injury", *Basic Res Cardiol 101* 2006, 53-60.
Lundin, Ronny H. "A convenient Method for the Synthesis of Peptide Trisulfides", *Tetrahedron Letters* vol. 35, No. 34 1994, 6339-6342.
Mott, Andrew W. "A New Method for the Synthesis of Unsymmetrical Trisulfanes", *Synthesis Communications* (8) 1984, 657-660.
Qu, Kun "Hydrogen Sulfide Is a Mediator of Cerebral Ischemic Damage", *Stroke*, 37 2006, 889-893.
Srilatha, Balasubramanian "Possible role for the novel gasotransmitter hydrogen sulphide in erectile dysfunction—a pilot study", *European Journal of Pharmacology 535* 2006, 280282.
Wintner, Edward A. "A monobromobimane-based assay to measure the pharmacokinetic profile of reactive sulphide species in blood", *BJP*, 160 2010, 941-957.
Wu, Sheng-Ying "Hydrogen sulfide ameliorates vascular calcification induced by vitamin D3 plus nicotine in rats", *Acta Pharmacologica Sinica 27*(3) Mar. 2006, 299-306.
Zanardo, Renata C. "Hydrogen sulfide is an endogenous modulator of leukocyte-mediated inflammation", *The FASEB Journal 20* 2006, 2118-2120.

*Primary Examiner* — Taofiq A Solola

(57) ABSTRACT

Compositions and methods of treating or preventing disease or injury to a human patient or biological material undergoing ischemic or hypoxic conditions.

8 Claims, 13 Drawing Sheets

* p<0.05 by 2-tailed t-test vs vehicle control

COMPOUNDS, COMPOSITIONS AND METHODS FOR TREATING OR PREVENTING HYPOXIC OR ISCHEMIC INJURY

CROSS-REFERENCE TO RELATED APPLICATIONS

This application claims priority under 35 U.S.C. §119(e) to U.S. patent application Ser. No. 61/303,532, filed Feb. 11, 2010, which is hereby incorporated by reference in its entirety.

BACKGROUND

Treatment with hydrogen sulfide ($H_2S$) protects biological matter from hypoxic and ischemic injury using a stable composition of hydrogen sulfide in mammals. (US Pub. No. 2008/0199541). This discovery provides exciting possibilities for the treatment or prevention of a number of animal and human diseases, particularly hypoxia and ischemia-related diseases and injuries using sulfide compounds.

The present invention meets this need by providing pharmaceutical compositions which are demonstrated herein to protect animals from injury and death resulting from hypoxic and/or ischemic conditions, as well as other injuries and disease conditions.

SUMMARY

An aspect of the invention is a compound according to the structure (I):

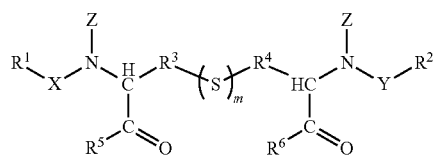

or a specific stereoisomer thereof according to the structure:

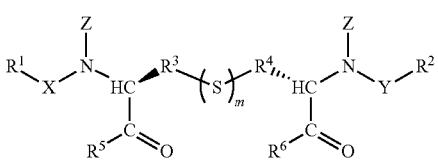

wherein $R^1$ and $R^2$ are independently a branched or straight chain $C_{1-10}$ alkyl; a branched or straight chain $C_{1-10}$ alkyl substituted with $-ONO_2$; or, a branched or straight chain $C_{1-10}$ alkyl substituted with $-OH$; wherein $R^3$ and $R^4$ are independently a branched or straight chain $C_{1-10}$ alkanediyl; wherein $R^5$ and $R^6$ are independently OH, an amino acid moiety, or, a straight or branched chain $C_{1-10}$ amine substituted with $-ONO_2$; wherein X and Y are independently C=O or $SO_2$; and, wherein m is 3 or 4; Z is selected from H, $CH_3$, and $CH_2CH_3$; or, a salt, ester, hydrate, solvate, or stereoisomer thereof, with the proviso that when m is 3, Z is H, X and Y are C=O, $R^3$ and $R^4$ are $CH_2$, and $R^5$ and $R^6$ are OH, then $R^1$ and $R^2$ are not $C_{1-10}$ alkyl. The polysulfide compound may be symmetrical or asymmetrical. The compound is an active pharmaceutical ingredient (API) useful in various forms of treatment as set forth herein.

Another aspect of the invention is a pharmaceutical composition comprising a therapeutically effective dose of a compound according to the structure (I)

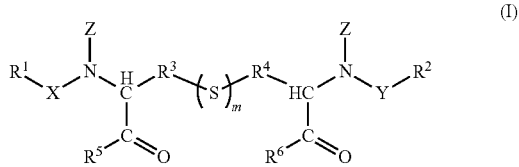

or a specific stereoisomer thereof according to the structure:

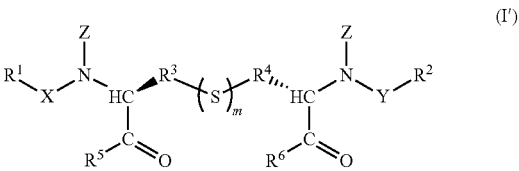

wherein $R^1$ and $R^2$ are independently a branched or straight chain $C_{1-10}$ alkyl; a branched or straight chain $C_{1-10}$ alkyl substituted with $-ONO_2$; or, a branched or straight chain $C_{1-10}$ alkyl substituted with $-OH$; wherein $R^3$ and $R^4$ are independently a branched or straight chain $C_{1-10}$ alkanediyl; wherein $R^5$ and $R^6$ are independently OH, an amino acid moiety, or, a straight or branched chain $C_{1-10}$ amine substituted with $-ONO_2$; wherein X and Y are independently C=O or $SO_2$; and, wherein m is 3 or 4; Z is selected from H, $CH_3$, and $CH_2CH_3$; or, a salt, ester, hydrate, solvate, or stereoisomer thereof, and, a carrier system comprising one or more inactive pharmaceutical ingredients, wherein the pharmaceutical composition has a pH of 4.0-7.0 or 5.0-6.5.

Another aspect of the invention is a method for treating or preventing injury to a biological material exposed to hypoxic or ischemic conditions comprising parenterally administering to the biological material or a patient in need thereof a therapeutically effective dose of a compound according to the structure (I):

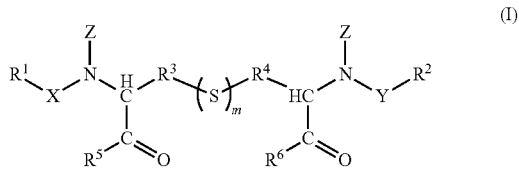

or a specific stereoisomer thereof according to the structure:

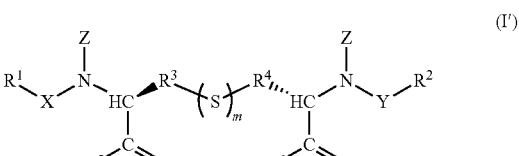

wherein $R^1$ and $R^2$ are independently a branched or straight chain $C_{1-10}$ alkyl; a branched or straight chain $C_{1-10}$ alkyl substituted with —ONO$_2$; or, a branched or straight chain C$_{1-10}$ alkyl substituted with —OH; wherein R$^3$ and R$^4$ are independently a branched or straight chain C$_{1-10}$ alkanediyl; wherein R$^5$ and R$^6$ are independently OH, an amino acid moiety, or, a straight or branched chain C$_{1-10}$ amine substituted with —ONO$_2$; wherein X and Y are independently C=O or SO$_2$; and, wherein m is 3 or 4; Z is selected from H, CH$_3$, and CH$_2$CH$_3$; or, a salt, ester, hydrate, solvate or stereoisomer thereof.

Another aspect of the invention is a method of making an intravenous or subcutaneous dosage form comprising a) providing a compound according to the structure (I):

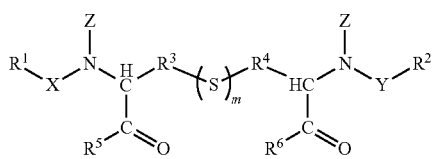

or a specific stereoisomer thereof according to the structure:

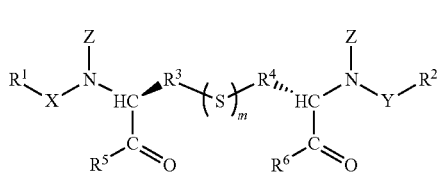

wherein R$^1$ and R$^2$ are independently a branched or straight chain C$_{1-10}$ alkyl; a branched or straight chain C$_{1-10}$ alkyl substituted with —ONO$_2$; or, a branched or straight chain C$_{1-10}$ alkyl substituted with —OH; wherein R$^3$ and R$^4$ are independently a branched or straight chain C$_{1-10}$ alkanediyl; wherein R$^5$ and R$^6$ are independently OH, an amino acid moiety, or, a straight or branched chain C$_{1-10}$ amine substituted with —ONO$_2$; wherein X and Y are independently C=O or SO$_2$; and, wherein m is 3 or 4; Z is selected from H, CH$_3$, and CH$_2$CH$_3$; or, a salt, ester, hydrate, solvate or stereoisomer thereof; b) making a vehicle solution by mixing a solution of 1% citric acid in sterile water with saline, and adding 0.5N NaOH in saline to adjust the pH to 5.5-6.5; c) dissolving the pre-determined amount of the compound in the vehicle solution; d) readjusting the pH of this compound-containing solution back to 5.0-6.5 or 4.0-7.0 by adding NaOH while stirring; e) and adding a defined second amount of the vehicle solution to produce an intravenous or subcutaneous dosage form having a predetermined dose concentration.

Another aspect of the invention is a compound according to the structure (II):

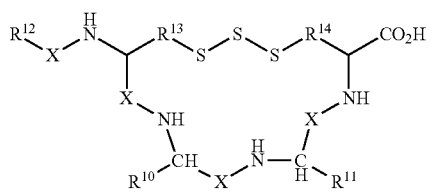

or a specific stereoisomer thereof according to the structure:

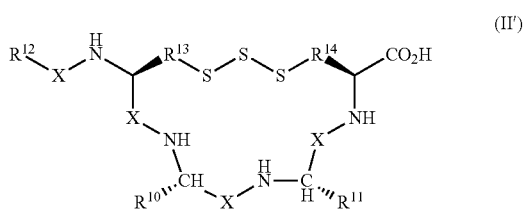

wherein R$^{10}$, R$^{11}$ and R$^{12}$ are each independently a side chain of a naturally-occurring or a non-naturally occurring amino acid (e.g., CH$_2$CO$_2$H, (CH$_2$)$_2$CO$_2$H), a branched or straight chain C$_{1-10}$ alkyl, a straight or branched chain C$_{1-10}$ alkyl substituted with —ONO$_2$, or, a straight or branched chain C$_{1-10}$ alkyl substituted with —OH; wherein R$^{13}$ and R$^{14}$ are independently a branched or straight chain C$_{1-10}$ alkanediyl; and, wherein X is independently C=O or SO$_2$; or, a salt, ester, hydrate, solvate or stereoisomer thereof.

Another aspect of the invention is a pharmaceutical composition comprising a therapeutically effective dose of a compound according to the structure (II):

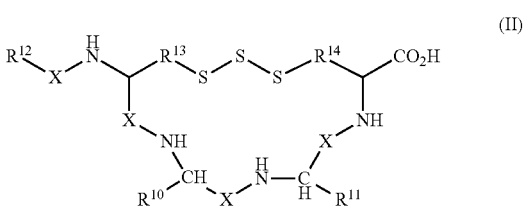

or a specific stereoisomer thereof according to the structure:

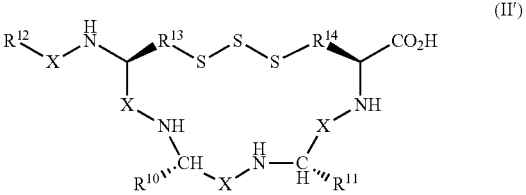

wherein R$^{10}$, R$^{11}$ and R$^{12}$ are independently a side chain of a naturally-occurring or a non-naturally occurring amino acid (e.g., CH$_2$CO$_2$H, (CH$_2$)$_2$CO$_2$H), a branched or straight chain C$_{1-10}$ alkyl, a straight or branched chain C$_{1-10}$ alkyl substituted with —ONO$_2$, or, a straight or branched chain C$_{1-10}$ alkyl substituted with —OH; wherein R$^{13}$ and R$^{14}$ are independently a branched or straight chain C$_{1-10}$ alkanediyl; and, wherein X is independently C=O or SO$_2$; or, a salt, ester, hydrate, solvate or stereoisomer thereof; and, a parenteral carrier system comprising one or more inactive pharmaceutical ingredients, wherein the pharmaceutical composition has a pH of 4.0-7.0 or 5.0-6.5.

Another aspect of the invention is a method for treating or preventing injury to a biological material exposed to hypoxic or ischemic conditions comprising parenterally administering to the biological material or a patient in need thereof a therapeutically effective dose of a compound according to the structure (II):

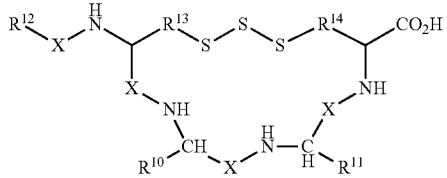

(II)

or a specific stereoisomer thereof according to the structure:

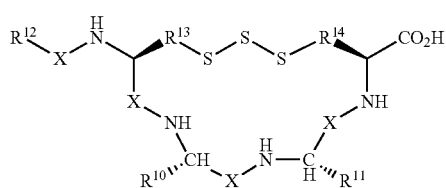

(II')

wherein $R^{10}$, $R^{11}$ and $R^{12}$ are independently a side chain of a naturally-occurring or a non-naturally occurring amino acid (e.g., $CH_2CO_2H$, $(CH_2)_2CO_2H$), a branched or straight chain $C_{1-10}$ alkyl, a straight or branched chain $C_{1-10}$ alkyl substituted with —$ONO_2$, or, a straight or branched chain $C_{1-10}$ alkyl substituted with —OH; wherein $R^{13}$ and $R^{14}$ are independently a branched or straight chain $C_{1-10}$ alkanediyl; and, wherein X is independently C=O or $SO_2$; or, a salt, ester, hydrate, solvate or stereoisomer thereof.

Another aspect of the invention is a compound according to the structure (III):

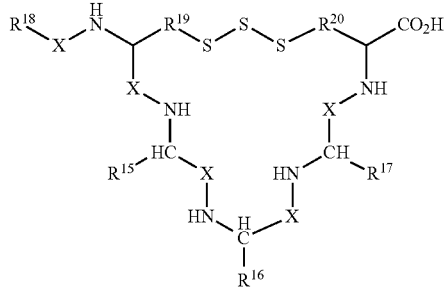

(III)

or a specific stereoisomer thereof according to the structure:

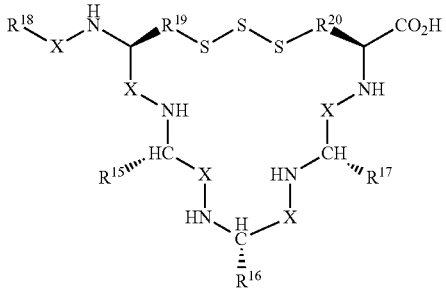

(III')

wherein $R^{15}$, $R^{16}$, $R^{17}$ and $R^{18}$ are each independently a side chain of a naturally-occurring or a non-naturally occurring amino acid (e.g., $CH_2CO_2H$, $(CH_2)_2CO_2H$), a branched or straight chain $C_{1-10}$ alkyl, a straight or branched chain $C_{1-10}$ alkyl substituted with —$ONO_2$, or, a straight or branched chain $C_{1-10}$ alkyl substituted with —OH; wherein $R^{19}$ and $R^{20}$ are each independently a branched or straight chain $C_{1-10}$ alkanediyl; and, wherein each X is independently C=O or $SO_2$; or, a salt, ester, hydrate, solvate, or stereoisomer thereof.

Another aspect of the invention is a pharmaceutical composition comprising a therapeutically effective dose of a compound according to the structure (III):

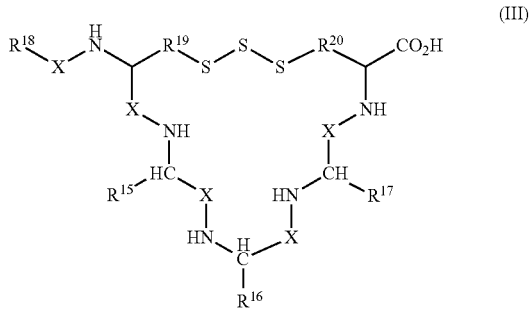

(III)

or a specific stereoisomer thereof according to the structure:

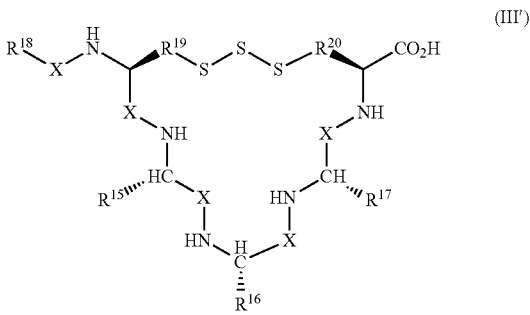

(III')

wherein $R^{15}$, $R^{16}$, $R^{17}$ and $R^{18}$ are independently a side chain of a naturally-occurring or a non-naturally occurring amino acid (e.g., $CH_2CO_2H$, $(CH_2)_2CO_2H$), a branched or straight chain $C_{1-10}$ alkyl, a straight or branched chain $C_{1-10}$ alkyl substituted with —$ONO_2$, or, a straight or branched chain $C_{1-10}$ alkyl substituted with —OH; wherein $R^{19}$ and $R^{20}$ are independently a branched or straight chain $C_{1-10}$ alkanediyl; and, wherein X is independently C=O or $SO_2$; or, a salt, ester, hydrate, solvate, or stereoisomer thereof; and, a parenteral carrier system comprising one or more inactive pharmaceutical ingredients, wherein the pharmaceutical composition has a pH of 4.0-7.0 or 5.0-6.5.

Another aspect of the invention is a method for treating or preventing injury to a biological material exposed to hypoxic or ischemic conditions comprising parenterally administering to the biological material or a patient in need thereof a therapeutically effective dose of a compound according to the structure (III):

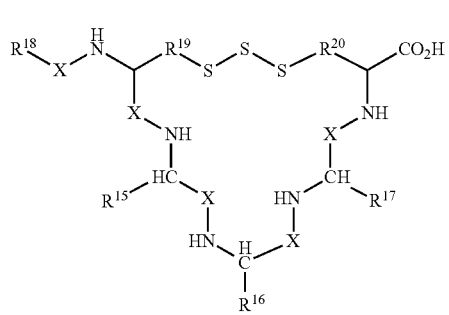

(III)

or a specific stereoisomer thereof according to the structure:

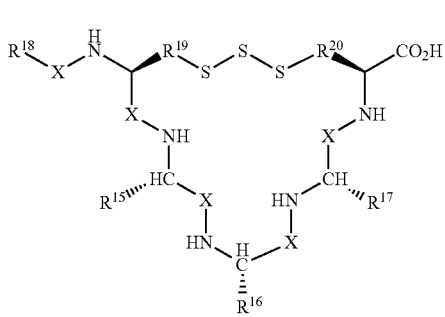

(III')

wherein $R^{15}$, $R^{16}$, $R^{17}$ and $R^{18}$ are independently a side chain of a naturally-occurring or a non-naturally occurring amino acid (e.g., $CH_2CO_2H$, $(CH_2)_2CO_2H$), a branched or straight chain $C_{1-10}$ alkyl, a straight or branched chain $C_{1-10}$ alkyl substituted with $-ONO_2$, or, a straight or branched chain $C_{1-10}$ alkyl substituted with $-OH$; wherein $R^{19}$ and $R^{20}$ are independently a branched or straight chain $C_{1-10}$ alkanediyl; and, wherein X is independently $C=O$ or $SO_2$; or, a salt, ester, hydrate, solvate, or stereoisomer thereof.

In an exemplary embodiment of the compound (I), its pharmaceutical compositions, its methods of making and its methods of use for treating or preventing injury to a biological material, m is 3, Z is H, and $R^5$ and $R^6$ are OH according to the free acid structure

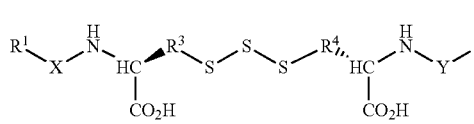

(I-a)

or, a salt, ester, hydrate, or solvate thereof.

In another exemplary embodiment of the compound (I), its pharmaceutical compositions, its methods of making and its methods of use for treating or preventing injury to a biological material, $R^3$ and $R^4$ are selected from $C(CH_3)_2$, $CH(CH_3)$, $(CH_2)_2$, and $CH_2$, Z is H, and, $R^5$ and $R^6$ are selected from $NHCH_2COOH$, $NH(CH_2)_2COOH$, $NHCH_2ONO_2$, $NH(CH_2)_2ONO_2$, and $NH(CH_2)_2OH$.

In another exemplary embodiment of the compound (I), its pharmaceutical compositions, its methods of making and its methods of use for treating or preventing injury to a biological material, X and Y are $SO_2$, Z is H, $R^1$ and $R^2$ are $CH_3$, $R^3$ and $R^4$ are $CH_2$, and, $R^5$ and $R^6$ are OH according to the free acid structure

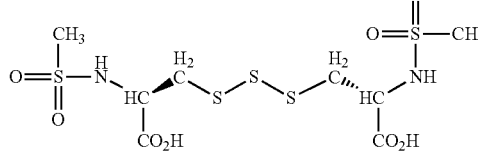

(I-d)

or, a salt, ester, hydrate, or solvate thereof.

In another exemplary embodiment of the compound (I), its pharmaceutical compositions, its methods of making and its methods of use for treating or preventing injury to a biological material, X and Y are $C=O$, Z is H, $R^1$ and $R^2$ are $CH_3$, $R^3$ and $R^4$ are $C(CH_3)_2$, and, $R^5$ and $R^6$ are OH according to the free acid structure

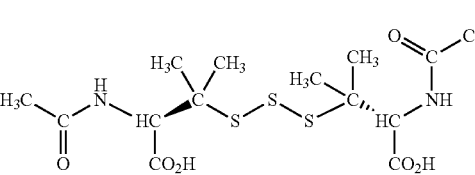

(I-c)

or, a salt, ester, hydrate, or solvate thereof.

In another exemplary embodiment of the compound (I), its pharmaceutical compositions, its methods of making and its methods of use for treating or preventing injury to a biological material, X and Y are $C=O$, Z is H, $R^1$ and $R^2$ are $CH_3$, $R^3$ and $R^4$ are $(CH_2)_2$, and, $R^5$ and $R^6$ are OH according to the free acid structure

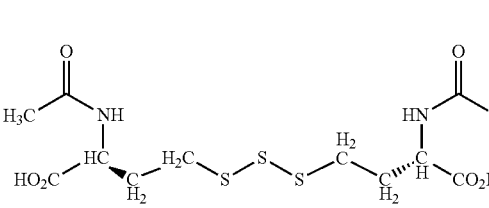

(I-b)

or, a salt, ester, hydrate, or solvate thereof.

In another exemplary embodiment of the compound, its pharmaceutical compositions, its methods of making and its methods of use for treating or preventing injury to a biological material, X and Y are $C=O$, $R^1$ and $R^2$ are $CH_3$, $R^3$ and $R^4$ are $CH_2$, Z is $CH_3$, and, $R^5$ and $R^6$ are OH according to the free acid structure

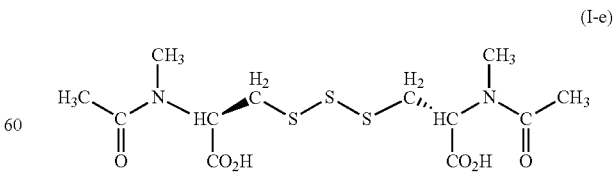

(I-e)

or, a salt, ester, hydrate, or solvate thereof.

In another exemplary embodiment of the compound (I), its pharmaceutical compositions, its methods of making and its methods of use for treating or preventing injury to a biological material, X and Y are C=O, Z is H, $R^1$ and $R^2$ are $CH_3$, $R^3$ and $R^4$ are $CH_2$, and, $R^5$ and $R^6$ are $NHCH_2CO_2H$ according to the free acid structure (I-f)

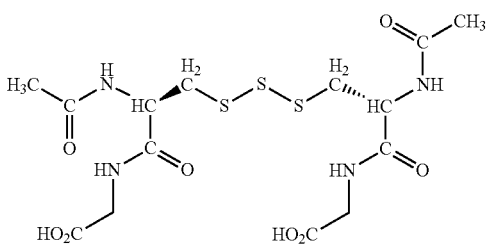

or, a salt, ester, hydrate, or solvate thereof.

In another exemplary embodiment of the compound (I), its pharmaceutical compositions, its methods of making and its methods of use for treating or preventing injury to a biological material, X and Y are C=O, Z is H, $R^1$ is $CH_3$, $R^2$ is $CH_2CH_3$, $R^3$ and $R^4$ are $CH_2$, and, $R^5$ and $R^6$ are OH according to the free acid structure (I-g)

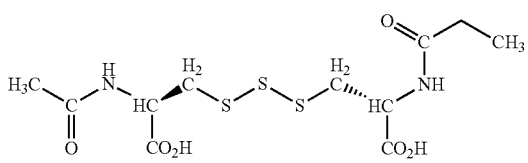

or, a salt, ester, hydrate, or solvate thereof.

In another exemplary embodiment of the compound (I), its pharmaceutical compositions, its methods of making and its methods of use for treating or preventing injury to a biological material, X is C=O, Y is $SO_2$, Z is H, $R^1$ and $R^2$ are $CH_3$, $R^3$ and $R^4$ are $CH_2$, and, $R^5$ and $R^6$ are OH according to the free acid structure (I-j)

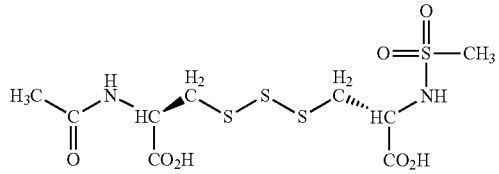

or, a salt, ester, hydrate, or solvate thereof.

In another exemplary embodiment of the compound (I), its pharmaceutical compositions, its methods of making and its methods of use for treating or preventing injury to a biological material, X and Y are C=O, Z is H, $R^1$ and $R^2$ are $CH_3$, $R^3$ is $CH_2$, $R^4$ is $C(CH_3)_2$, and, $R^5$ and $R^6$ are OH according to the free acid structure (I-k)

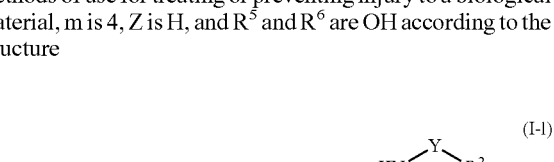

or, a salt, ester, hydrate, or solvate thereof.

In another exemplary embodiment of the compound (I), its pharmaceutical compositions, its methods of making and its methods of use for treating or preventing injury to a biological material, X and Y are C=O, Z is H, $R^1$ and $R^2$ are $CH_3$, $R^3$ and $R^4$ are $CH_2$, $R^5$ is OH, and, $R^6$ is $NHCH_2CO_2H$ according to the free acid structure (I-h)

or, a salt, ester, hydrate, or solvate thereof.

In another exemplary embodiment of the compound (I), its pharmaceutical compositions, its methods of making and its methods of use for treating or preventing injury to a biological material, X and Y are C=O, Z is H, $R^1$ and $R^2$ are $CH_3$, $R^3$ and $R^4$ are $CH_2$, $R^5$ is OH, and, $R^6$ is $NH(CH_2)_2ONO_2$ according to the structure (I-i)

or, a salt, ester, hydrate, or solvate thereof.

In another exemplary embodiment of the compound (I), its pharmaceutical compositions, its methods of making and its methods of use for treating or preventing injury to a biological material, m is 4, Z is H, and $R^5$ and $R^6$ are OH according to the structure (I-l)

or, a salt, ester, hydrate, or solvate thereof.

In another exemplary embodiment the pharmaceutical composition is made by mixing the compound in a carrier of water; NaCl; a weak acid such as mono, di, or tricarboxylic acid (e.g., citric acid); and NaOH.

In another exemplary embodiment the pharmaceutical composition the carrier is a sodium phosphate buffer of pH 4-7.

In another exemplary embodiment of the pharmaceutical composition, the citric acid comprises in the range of 0.01% to 2% of the intravenous carrier system.

In another exemplary embodiment of the pharmaceutical composition, the citric acid comprises in the range 0.05% to 0.1% of the intravenous carrier system.

In another exemplary embodiment of the pharmaceutical composition, the pH of the intravenous dosage form is in the range of 5.0-6.5 or 4.0-7.0.

In another exemplary embodiment of the pharmaceutical composition, the effective dose is in the range of 0.1 to 100 mg/Kg, 0.1 to 200 mg/Kg, 5 to 100 mg/Kg or 2 to 60 mg/Kg based on body weight.

In another exemplary embodiment, the pharmaceutical composition is a parenteral or other dosage form selected from intravenous, injection, infusion, continuous infusion, intradermal, intraarterial, intracerebral, intracerebroventricular, intracardiac, intraosseous infusion, intralesional, intracranial, intraprostatical, intrapleural, intratracheal, intranasal, intravitreal, intravaginal, intrarectal, intratumoral, intramuscular, intraocular, intrathecal, subcutaneous, subconjunctival, transmucosal, intramuscular, intravesicular, intravesical, intracavernosal injection, intrapericardial, intraumbilical, intraocularal, absorption, adsorption, immersion, localized perfusion, intracisternal, bolus and epidural.

In another exemplary embodiment of the methods of treating according to the invention, the compound is administered in a parenteral dosage form comprising the compound, and, a parenteral carrier system or vehicle solution comprising one or more inactive pharmaceutical ingredients.

In another exemplary embodiment of the methods of treating according to the invention, the compound is administered intravenously in an intravenous dosage form, as a single bolus, as a repeat bolus or as a continuous infusion.

In another exemplary embodiment of the methods of treating according to the invention, m is 4, and the compound is administered in an intravenous dosage form comprising the compound and a parenteral carrier system, which comprises one or more inactive pharmaceutical ingredients, accordingly.

In another exemplary embodiment of the methods of treating according to the invention, the method further comprises continuously or intermittently administering the intravenous or other parenteral dosage form for a duration of 1 minute to 2 days or 1 to 5 hours.

In another exemplary embodiment of the methods of treating according to the invention, the method further comprises administering a predetermined plurality of doses over a specified interval, for example, administering a dosing regimen of the intravenous dosage form, wherein the dosing regimen comprises a predetermined plurality of doses over a predetermined duration at predetermined intervals.

In another exemplary embodiment of the methods of treating according to the invention, the method further comprises administering a dosing regimen of the intravenous or other parenteral dosage form, wherein the dosing regimen comprises continuously administering a predetermined dose over a predetermined duration.

In another exemplary embodiment of the methods of treating according to the invention, the hypoxic or ischemic condition results from an injury to the biological material, the onset or progression of a disease which adversely affects the biological material or hemorrhaging of the biological material.

In another exemplary embodiment of the methods of treating according to the invention, the biological material is contacted with the compound before the injury, before the onset or progression of the disease, or before hemorrhaging of the biological material.

In another exemplary embodiment of the methods of treating according to the invention, the injury is from an external physical source, such as surgery.

In another exemplary embodiment of the methods of treating according to the invention, the hypoxic or ischemic conditions result in myocardial infarction, sepsis, vascular abnormalities, cirrhosis, liver injury, kidney injury, vascular calcification, gastric injury induced by drug treatment, burns, lung injury, neutrophil adhesion, leukocyte-mediated inflammation, erectile dysfunction, irritable bowel syndrome, antinociceptive effects in post-inflammatory hypersensitivity, acute coronary syndrome, cardiac arrest, planned cardiac bypass surgery, congestive heart failure, neonatal hypoxia/ischemia, myocardial ischemic reperfusion injury, unstable angina, post-angioplasty, aneurysm, trauma, stroke, hemorrhagic shock, and/or blood loss.

In an exemplary embodiment of the methods of making the pharmaceutical compositions of the compounds of the invention, the vehicle solution is made by mixing 1 volume of 0.5N NaOH in saline (0.9% NaCl injection solution, Baxter), 4 volumes of 1% citric acid in sterile water, and 36 volumes of saline. The pH of the resulting vehicle solution is about 6.

In another exemplary embodiment of the methods of making the pharmaceutical compositions of the compounds of the invention, the predetermined concentration of the dosing solution is in the range of 0.1 to 200 mg/mL, 1 to 100, or even 2 to 40 mg/mL, or even 5 to 6 mg/mL and the administered dose in the range of 0.1 to 200 mg/Kg, or even 2 to 60 mg/Kg, or even specifically 20 mg/Kg, based on body weight.

In a further exemplary embodiment of the methods of making the pharmaceutical compositions of the invention, a predetermined volume of dosing solution of bis-N-acetyl-cystine-trisulfide at a predetermined concentration between 2 and 40 mg/mL is prepared by weighing the calculated amount of solid bis-N-acetyl-cystine-trisulfide into a clear glass vial and chilling the vial to −20° C. The required volume of solvent is prepared by diluting 0.011 mL of 0.5N NaOH in saline for every 1 mg of bis-N-acetyl-cystine-trisulfide with a suitable volume of above vehicle solution such that the predetermined volume of dosing solution is reached. The entire amount of solvent is mixed to homogeneity, chilled to between 0° C. and 4° C. and added to the vial of bis-N-acetyl-cystine-trisulfide. The resulting suspension is mixed immediately until the solid is fully dissolved.

In one more exemplary embodiment of the methods of making the pharmaceutical compositions of the invention, a dosing solution of bis-N-acetyl-cystine-trisulfide at 30 mg/mL is prepared by weighing the desired amount of solid bis-N-acetyl-cystine-trisulfide into a clear glass vial and chilling the vial to −20° C. The solvent is prepared by chilling a suitable amount of a mixture of 1 volumes of 0.5N NaOH in saline and 2 volumes of above vehicle solution to between 0° C. and 4° C. One mL of this solvent is added to the vial per 30 mg of bis-N-acetyl-cystine-trisulfide contained and the resulting suspension mixed immediately until the solid is fully dissolved. This dosing solution of bis-N-acetyl-cystine-trisulfide is stable for at least 1.5 hours at room temperature and for at least 24 hours when frozen at −20° C. The dosing solution is warmed to room temperature prior to intravenous injection.

DESCRIPTION OF DRAWINGS OF EXEMPLARY EMBODIMENTS

FIG. 1 is a graph demonstrating the pharmacokinetics of biologically available blood sulfide measured after intravenous administration of bis-N-acetyl-cystine-trisulfide at two doses (16 mg/kg and 32 mg/kg). Sulfide levels after IV bolus of vehicle are shown for comparison. Biologically available sulfide was measured by derivatization with mono-bromo-bimane (Wintner et al. 2010, Br. J. Pharmacology 160:941-957). Sulfide was elevated 1 min after IV bolus administration and decreased thereafter.

FIG. 2 is a graph demonstrating the pharmacokinetics of biologically available sulfide in blood as measured by derivatization with mono-bromo-bimane and of plasma thiosulfate after intravenous administration of bis-N-acetyl-cystine-trisulfide as a 32 mg/kg bolus compared to administration of vehicle. Plasma thiosulfate was measured by ion chromatography. Thiosulfate levels in blood paralleled blood levels of biologically available sulfide.

FIG. 3 is a graph demonstrating the pharmacokinetics of free sulfide in blood measured with a sulfide-specific electrode implanted in the vena cava of rats receiving an IV bolus of 20 mg/kg bolus dose of bis-N-acetyl-cystine-trisulfide or vehicle. Free sulfide levels were measured every second and are shown in minute intervals with breathing artifacts removed. No free sulfide was detectable.

FIG. 4 shows two bar graphs demonstrating the protection of the livers of mice from injury by dGal/LPS by an intraperitoneal (IP) bolus of bis-N-acetyl-cystine-trisulfide of 20 mg/kg given 30 min after LPS, compared to vehicle administration. Liver injury was monitored by levels of serum alanine transaminase (ALT), FIG. 4A, and serum aspartate aminotransferase (AST), FIG. 4B. Bis-N-acetyl-cystine-trisulfide reduced liver injury.

FIG. 5 is a bar graph demonstrating the protection of the livers of mice from injury by dGal/LPS by an intraperitoneal bolus of bis-N-acetyl-cystine-trisulfide of 40 and 60 mg/kg given 30 min after LPS, compared to vehicle administration. Hepatic injury was determined by measuring serum ALT. Bis-N-acetyl-cystine-trisulfide reduced liver injury.

FIG. 6 is a graph demonstrating that biologically available blood sulfide and plasma thiosulfate levels can be manipulated by repeated IV injections to achieve elevated exposure levels. Increased mono-bromo-bimane-reactive blood sulfide and blood thiosulfate levels persisted for 3 hours after administration of two consecutive IV boli of bis-N-acetyl-cystine-trisulfide at 0 and 15 min, compared to administration of vehicle.

Figure 9:
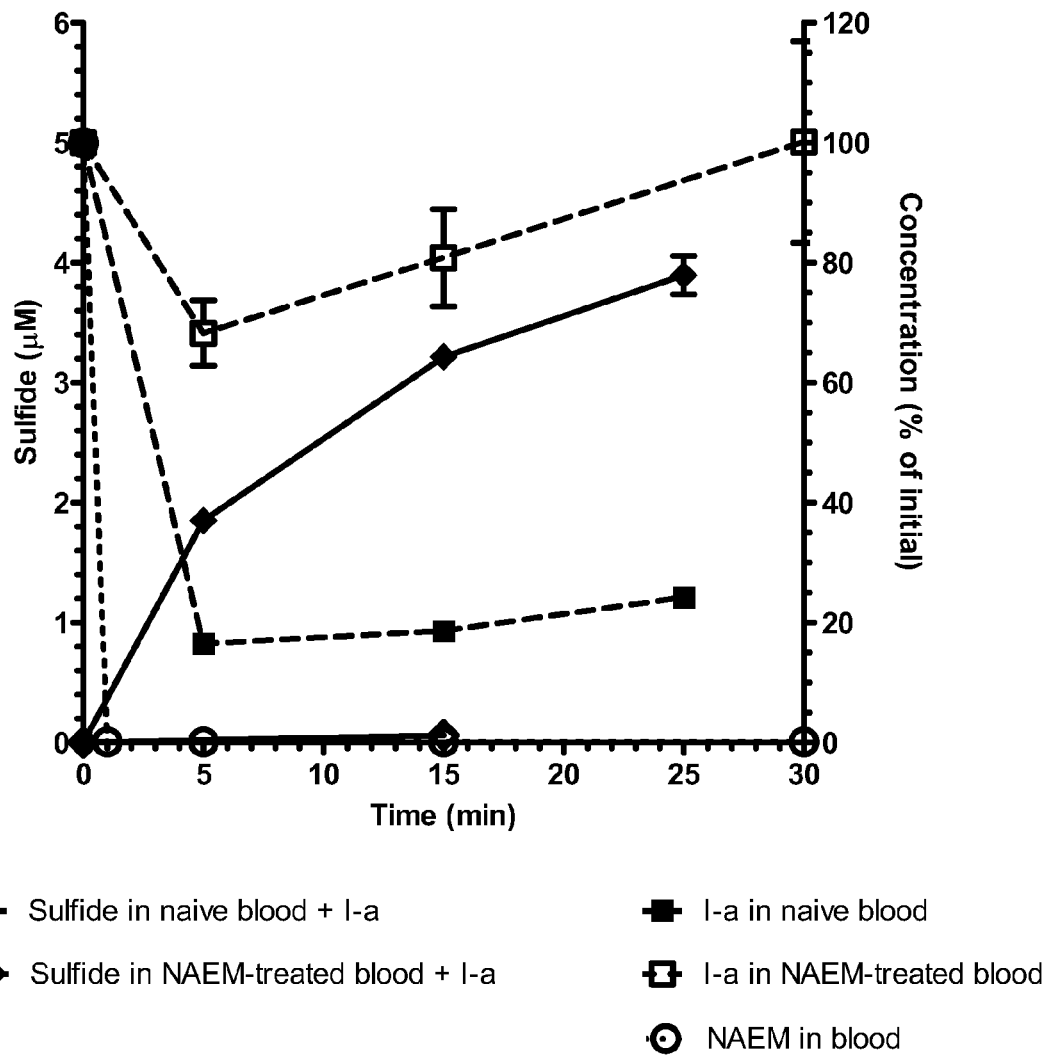

FIG. 9 is a graph demonstrating that blocking free thiols and perthiols in rat blood with the thiol-reactive agent N-aminoethyl-maleimide (NAEM) reduces the generation of biologically available sulfide. The concentration of biologically available blood sulfide is shown on the left y-axis, concentrations of bis-N-acetyl-cystine-trisulfide and NAEM are shown on the right y-axis relative to their initial concentrations. Time after bis-N-acetyl-cystine-trisulfide addition (sulfide and bis-N-acetyl-cystine-trisulfide curves) or NAEM addition (NAEM curve) shown on x-axis. Bis-N-acetyl-cystine-trisulfide and NAEM were measured in blood by LC/MS/MS, biologically available sulfide by derivatization with mono-bromo-bimane.

Figure 10A:
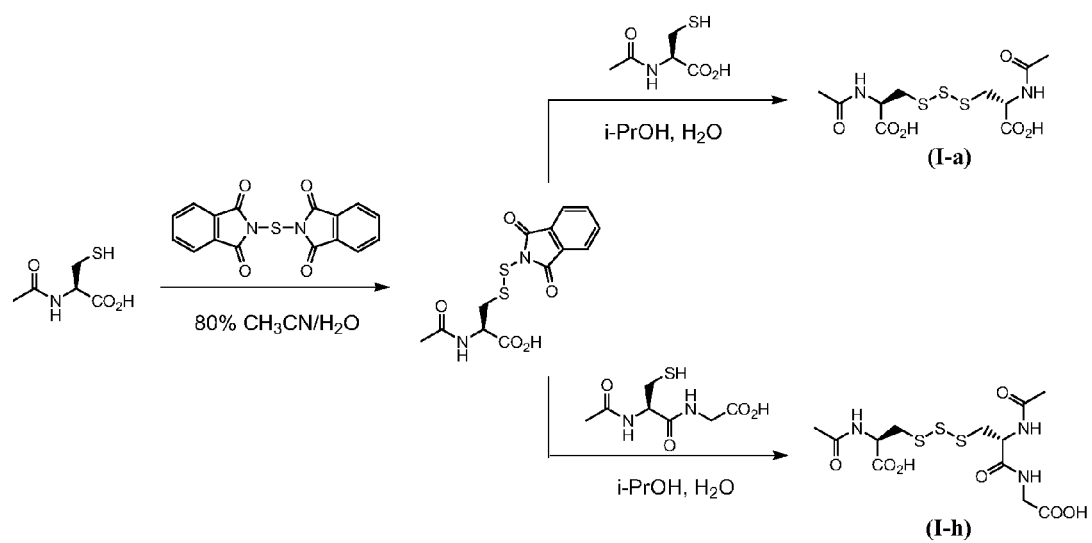
Figure 10B:
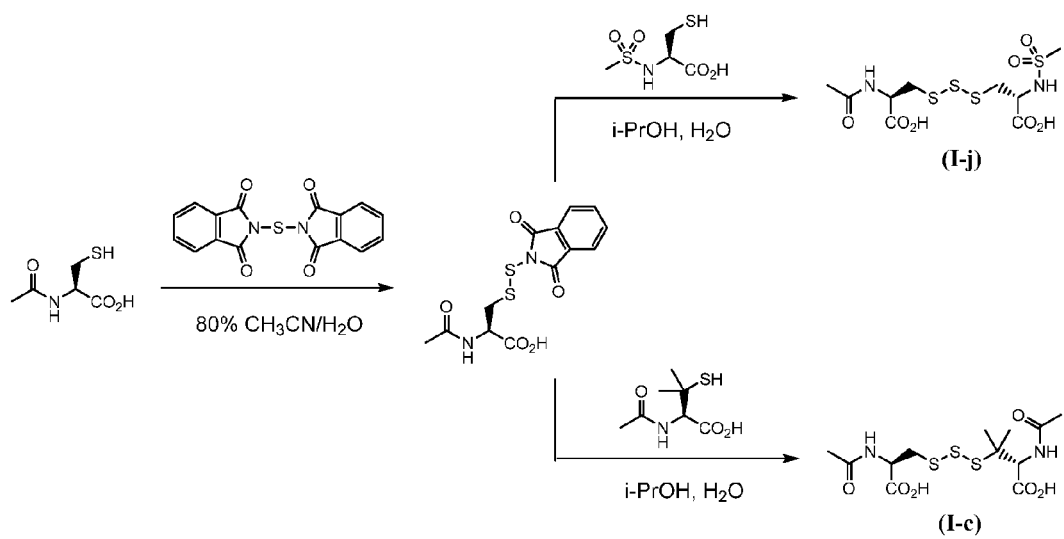
Figure 10C:
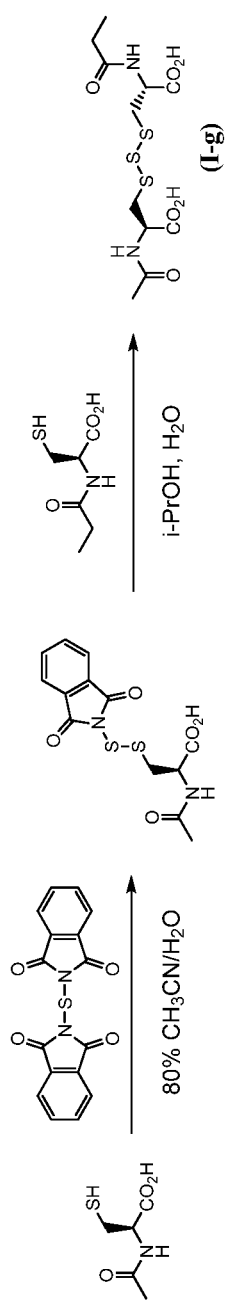

FIGS. 10A, 10B, and 10C are synthetic reactions according to Scheme 1 for preparation of embodiments of the present invention.

DETAILED DESCRIPTION OF THE EXEMPLARY EMBODIMENTS

In the following description, details are set forth to provide a more thorough and detailed description of various non-limiting exemplary embodiments.

The term "comprise" (and variations thereof) is to be construed as open, non-limiting, and open to the inclusion of other components, ingredients, steps or acts, and the like.

The terms "biological material" (and variations thereof) means mammalian (such as human) cells, tissues and organs, whereby it may be disposed within the organism, removed/isolated from the organism, or, on the whole of the organism.

The term "cell" (and variations thereof) refers to mammalian cells, such as from a human, monkey, mouse, rat, rabbit, hamster, goat, pig, dog, cat, ferret, cow, sheep, horse or the like. The cells may be diploid or haploid (i.e., sex cells). The cells may also be polyploid, aneuploid, or anucleate. The cell may be from a particular tissue or organ, such as heart, lung, kidney, liver, bone marrow, pancreas, skin, bone, vein, artery, cornea, blood, small intestine, large intestine, brain, spinal cord, smooth muscle, skeletal muscle, ovary, testis, uterus, umbilical cord or the like. The cell may also be a platelet, myelocyte, erythrocyte, lymphocyte, adipocyte, fibroblast, epithelial cell, endothelial cell, smooth muscle cell, heart muscle, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, sperm or the like.

The terms "tissue" and "organ" (and variations thereof) whereby "tissue" refers to an aggregate of similar cells forming a definite kind of structural material, and whereby "organ" refers to a particular type of tissue. The tissue or organ may be "isolated" from the subject or patient meaning that it is not located within the subject or patient or has been removed such.

The terms "hypoxia" and "hypoxic" (and variations thereof) refer to an environment having reduced dissolved oxygen content of a body of water detrimental to aerobic organisms or a pathological condition in which the body as a whole or region of the body is deprived of adequate oxygen supply. Hypoxia occurs when the normal physiologic levels of oxygen are not supplied to a cell, tissue, or organ.

The term "normoxia" (and variations thereof) refers to normal physiologic levels of oxygen for the particular cell type, cell state or tissue in question.

The term "anoxia" (and variations thereof) refers the absence of oxygen.

The term "hypoxic conditions" (and variations thereof) refer to conditions leading to cellular, organ or organismal hypoxia. Hypoxic conditions include conditions where the concentration of oxygen is at or less than normal atmospheric conditions. For example, the concentration of oxygen may be less than about any value in the range of 20.8% to 0.5%, or trace to undetectable concentrations, whereby the percentage may be that at 1 atmosphere of pressure (101.3 kPa).

The term "ischemia/reperfusion injury" denotes damage to tissues, vasculature, organs or body parts that is caused by the return of blood flow after a time period of oxygen deprivation resulting from ischemia. Reperfusion injury is caused both by the return of oxygen to ischemic tissues and by the inflammatory response solicited by tissues damaged by the return of circulation after the ischemic period. Return of blood flow exposes cells to oxygen which causes intracellular radical generation and damage to cellular proteins, DNA, and the plasma membrane. This can lead to calcium overload, energy failure and necrosis or the induction of apoptosis. In reperfusion injury, leukocytes (white blood cells) entering tissues and organs from the circulation release inflammatory mediators such as cytokines and interleukins, protease enzymes and free radicals that further damage the tissue or organ. Injured endothelium recruits leukocytes and platelets which can lead to obstruction of capillaries and further ischemia.

The term "ischemia" is a condition in which the blood flow (and oxygen) is restricted to a part of the body. Hypoxic or ischemic conditions may result from any one of the following: an injury to the biological material; the onset or progression of a disease that adversely affects the biological material; or, cardiac ischemia or hemorrhaging of the biological material. The biological material may be treated with the compounds of the invention (i.e., API) before the injury; before the onset or progression of the disease; before hemorrhaging of the biological material, or the like. The injury may be from an external physical force, such as surgery.

The terms "biologically available sulfide" (and variations thereof) refer to molecules detectable by derivatization with the chemical mono-bromo-bimane and measurement of the subsequently produced sulfide-di-bimane.

The terms "free sulfides" (and variations thereof) refer to sulfides that exist in an ionized or un-ionized state and are unbound and unsequestered by any protein, peptide or other molecule in the bloodstream. Free sulfides can be detected by the presence of exhaled H2S on an animal or patient's breath or by a membrane-mediated electrochemical probe which specifically measures unbound H2S molecules in solution. Free sulfide in the bloodstream can cause unwanted side effects.

The terms "inactive pharmaceutical ingredient" (and variations thereof) refer to any component of a drug product other than the active ingredient. (See 21 CFR 210.3(b)(8)).

The terms "active pharmaceutical ingredient" or "API" refer to any component of a drug product intended to furnish pharmacological activity or other direct effect in the diagnosis, cure, mitigation, treatment, or prevention of disease, or to affect the structure or any function of the body of humans or other animals. (See 21 CFR 210.3(b)(7)). APIs include those components of the product that may undergo chemical change during the manufacture of the drug product and be present in the drug product in a modified form intended to furnish the specified activity or effect. The polysulfide compounds, both linear and cyclic as well as symmetric and asymmetric, disclosed herein are APIs.

The term "dosage form" indicates a packaged form of the API suitable for administration as a medication or drug.

A "pharmaceutical composition" refers to a formulation of a compound (i.e., an API) of the invention and a medium generally accepted in the art for the delivery of the biologically active compound to mammals, e.g., humans. Such a medium (e.g., vehicle solution) includes all pharmaceutically acceptable carriers, diluents or excipients (i.e., inactive pharmaceutical ingredients) therefore. As used herein, the terms "vehicle solution" and "carrier system" (and variations of both) are used interchangeably.

The terms "complexing agent" refer to a molecule, typically an organic molecule, which binds a metal ion through two or more of the complexing agent's atoms.

The term "co-solvent" refers to any solvent or compound present in a mixture in addition to the primary solvent. Co-solvents are typically added to increase or decrease the solubility of the solutes.

The term "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another, and diastereomers, which are stereoisomers of compounds with more than one chiral center that are not enantiomers.

The compounds of the invention, or their pharmaceutically acceptable salts, may contain one or more asymmetric centers and may thus give rise to enantiomers, diastereomers, and other stereoisomeric forms that may be defined, in terms of absolute stereochemistry, as (R) or (S) or, as (D) or (L) for amino acids. The present invention is meant to include all such possible isomers, as well as their racemic and optically pure forms. Therefore, it is to be understood that where the structural representations of the inventive compounds set forth herein are shown as stereospecific it is for illustrative purposes only and the invention is not intended to be so limited.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft).

The term "alkyl" refers to a straight or branched chain hydrocarbon moiety. In one embodiment, the alkyl is $C_nH_{2n+1}$ where n is 1-10.

The term "alkanediyl" refers to a straight or branched chain divalent hydrocarbon moiety. In one embodiment, the alkanediyl is $C_nH_{2n}$ where n is 1-10.

The term "salts" (and variations thereof) of the instant compounds refer to pharmaceutically suitable (i.e., pharmaceutically acceptable) salts including, but not limited to, acid addition salts formed by mixing a solution of the instant compound with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with the instant compound such as those disclosed in Berge S M et al., "Pharmaceutical Salts." J. Pharm. Sci. 66:1-19 (1977) and Haynes D A et al., "Occurrence of pharmaceutically acceptable anions and cations in the Cambridge Structural Database," J. Pharm. Sci. 94:2111-2120 (2005), which are hereby incorporated herein by reference. For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

The term "hydrates" (and variations thereof) of the instant compounds refer to pharmaceutically suitable (i.e., pharmaceutically acceptable) hydrates being compounds formed by the addition of water or its elements to a host molecule (e.g., the free form version of the compound) including, but not limited to, monohydrates, dihydrates, etc.

The term "solvates" (and variations thereof) of the instant compounds refer to pharmaceutically suitable (i.e., pharmaceutically acceptable) solvates, whereby solvation is an interaction of a solute with the solvent which leads to stabilization of the solute species in the solution, and whereby the solvated state is an ion in a solution complexed by solvent molecules.

The invention disclosed herein is also meant to encompass all pharmaceutically acceptable versions of the compounds of the invention herein being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These compounds could be useful to help determine or measure the effectiveness of the compounds, by characterizing, for example, the site or mode of action, or binding affinity to pharmacologically important site of action. Certain isotopically-labelled versions of the compounds of the invention, for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

"Stable compound" and "stable structure" are meant to indicate a compound that is sufficiently robust to survive isolation to a useful degree of purity from a reaction mixture, and formulation into an efficacious therapeutic agent. As used herein, "stable" refers to the concentration of the active polysulfide composition, the pH of the polysulfide composition and/or any polysulfide degradation products remaining within a specified range.

Pharmaceutical compositions of the invention are administered by injection or infusion (e.g. intravenous, subcutaneous, etc.) and include, but are not limited to, liposomal injectables or a lipid bilayer vesicle having phospholipids that encapsulate an active drug substance. Injection includes a sterile preparation intended for parenteral use.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated. The terms "parenteral carrier system" (including variations thereof such as the various specific injectable and infusible dosage forms) refer to compositions comprising one or more pharmaceutically suitable excipients, such as solvents (e.g. water) and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient.

Five distinct classes of injectable dosage forms exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution.

Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for sterile suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections.

Suspension injection involves a liquid preparation (suitable for injection) containing insoluble solid and/or immiscible liquid particles dispersed throughout a liquid phase. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable (i.e., USP and FDA-approved) excipients and/or diluents, such as solvents and co-solvents, solubilizing agents, wetting agents, suspending agents, thickening agents, emulsifying agents, chelating agents, buffers, pH adjusters, antioxidants, reducing agents, antimicrobial preservatives or other preservatives, dispersing agents, surfactant, bulking agents, protectants, tonicity adjusters, emulsifiers, stabilizers, glidants, isotonic agents, and special additives.

The terms "therapeutically effective dose" (and variations thereof) refer to an amount, dose or dosing regimen of a compound (i.e., active pharmaceutical ingredient, prodrug or precursor thereof) that upon interaction with a biological material is sufficient to treat or prevent injury of a biological material (e.g., induce a measurable result) exposed to hypoxic or ischemic conditions, whereby such dose may vary depending on the form of the compound, the biological material's condition and/or severity, the route of administration, the age of the biological material, and the like.

"Therapeutically effective dose" may also mean a dose administered to a human subject/patient in a controlled Phase II or Phase III clinical trial that causes a statistically significant benefit on a predefined clinical endpoint (e.g., mortality). A therapeutically effective dose may also be a dose that enhances the survivability of biological matter in response to a disease or injury or an amount that induces stasis or pre-stasis in the biological matter.

The instant dosage form and routes of administration of a pharmaceutical composition include parenteral by injection or infusion (or other parenteral) such as intravenous, injection, infusion, continuous infusion, intradermal, intraarterial, intracerebral, intracerebroventricular, intracardiac, intraosseous infusion, intralesional, intracranial, intraprostatical, intrapleural, intratracheal, intranasal, intravitreal, intravaginal, intrarectal, intratumoral, intramuscular, intraocular, intrathecal, subcutaneous, subconjunctival, transmucosal, intramuscular, intravesicular, intravesical, intracavernosal injection, intrapericardial, intraumbilical, intraocularal, absorption, adsorption, immersion, localized perfusion, intracisternal, bolus and epidural.

The compounds of the invention may be administered to the biological material in a dose and for a duration sufficient to protect the biological material from one or more of the following: damage or death resulting from the injury; onset or progression of disease; hemorrhaging in the biological material, or the like.

The mammalian biological material may be one or more of the following: cells, tissues, organs, organisms or an animal. The mammal may be a human. The biological material may be platelets. The biological material may be used for transplantation. The biological material may be at risk of reperfusion injury. The biological material may also be at risk of hemorrhagic shock.

The hypoxic or ischemic conditions may result in one or more of the following: myocardial infarction, sepsis, vascular abnormalities, cirrhosis, liver injury, kidney injury, vascular calcification, gastric injury induced by drug treatment, burns, lung injury, neutrophil adhesion, leukocyte-mediated inflammation, erectile dysfunction, irritable bowel syndrome, anti-nociceptive effects in post-inflammatory hypersensitivity, acute coronary syndrome, cardiac arrest, planned cardiac bypass surgery, congestive heart failure, neonatal hypoxia/ischemia, myocardial ischemic reperfusion injury, unstable angina, post-angioplasty, aneurysm, trauma, stroke, hemorrhagic shock, and/or blood loss, or the like.

The compounds of the invention may be used to treat or prophylactically treat various diseases and disorders such as those disclosed in U.S. Patent Application Publication No. 2008/0199541. Other such treatable conditions include myocardial infarction, sepsis (Hui, et al. J Infect (2003) 47:155-160), congestive heart failure, vascular abnormalities in cirrhosis (Fiorucci S, et al., Hepatology (2005) 42:539-548), as a cardioprotectent (Geng, et al., Biochem Biophys Res Commun (2004) 313:362-368), as a neuroprotectant (Qu K. et al, Stroke (2006) 37:889-893), myocardial ischemia reperfusion injury (Johansen et al., Basic Res Cardiol (2006) 101:53-60), vascular calcification (Wu et al., Acta Pharmacol Sin. (2006) 27:299-306), gastric injury induced by drug treatment (Fiorucci, S. et al., Gastroenterology (2005) 129:1210-1224), neutrophil adhesion and modulation of leukocyte-mediated inflammation (Zanardo et al., FASEB J. (2006) 20:2118-2120), erectile dysfunction (Srilatha B. et al., Eur J Pharmacol. (2006) 535:280-282), irritable bowel syndrome (Distrutti E., et al., JPET (2006) 319:447-458), and, anti-nociceptive effects in post-inflammatory hypersensitivity (ibid.).

The compounds of the invention may also be used to treat or prophylactically treat to prevent injury to biological matter exposed to ischemic or hypoxic conditions. The compounds of the invention may be used to treat patients that have undergone, are undergoing, or, are susceptible to injury, trauma or critical care treatment. Injury may be caused by external insults, such as burns, wounds, amputations, gunshot wounds, surgical trauma, abdominal surgery, prostate surgery, limb surgery, internal insults (such as septic shock), stroke or cardiac arrest, heart attack that result in the acute reduction in circulation, reductions in circulation due to non-invasive stress (such as exposure to cold or radiation) or the like. At the cellular level, injury may result in exposure of cells, tissues and/or organs to hypoxia thereby resulting in induction of programmed cell death, or apoptosis.

The compounds of the invention may also be used for treating reperfusion injury such as edema through vascular leak and acute inflammation caused by penetration of activated leukocytes into tissue and cell death by necrosis and apoptosis, as well as other etiologies. Reperfusion injury can occur following myocardial reperfusion after an acute myocardial infarction, stroke, cardiac arrest, or coronary artery bypass graft (CABG) surgery. Reperfusion injury is noted following the transplantation of an organ or following resuscitation after hemorrhagic shock or severe bleeding in traumatized patients.

The compounds of the invention are also useful for preventing or treatment of hypoxic or ischemic injury related to transplantation of a tissue or an organ. The compounds of the invention are also useful in the prevention or treatment of delayed graft function.

The compounds of the invention are also useful for inducing tissue regeneration and wound healing by prevention/delay of biological processes that may result in delayed wound healing and tissue regeneration. In addition to wound healing, methods can be implemented to prevent or treat trauma such as cardiac arrest or stroke, and hemorrhagic shock. The compounds of the invention are also useful for reducing the risk of trauma from emergency surgical procedures, such as thoracotomy, laparotomy, and splenic transaction or cardiac surgery, aneurysm, surgery, brain surgery and the like. The compounds of the invention may also be used to prevent or treat injury resulting from Systemic Inflammatory Response Syndrome (SIRS), Acute Respiratory Distress Syndrome (ARDS), kidney failure, liver failure and multi-organ failure.

The compounds of the invention are also useful for methods of enhancing survivability and prevent ischemic injury resulting from cardiac arrest or stroke by providing a therapeutically effective amount of the composition to the patient before, after, or both before and after myocardial infarction, cardiac arrest or stroke.

The compounds of the invention may also be used to treat or prevent ischemia/reperfusion injury; an inflammatory disease or disorder; or, a vascular leak.

The compounds of the invention are also useful in methods of pre-treating a biological material, e.g., a patient, prior to an ischemic or hypoxic injury or disease insult. These methods can be used when an injury or disease with the potential to cause ischemia or hypoxia is scheduled or elected in advance, or predicted in advance to likely occur. Examples include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of organ donors prior to removal of donor organs for transport and transplantation into a recipient in need of an organ transplant. Examples include, but are not limited to, medical conditions in which a risk of injury or disease progression is inherent (e.g., in the context of unstable angina, following angioplasty, bleeding aneurysms, hemorrhagic strokes, following major trauma, hemorrhaging or blood loss), or in which the risk can be diagnosed using a medical diagnostic test.

The compounds of the invention may be formulated into various dosage forms for various routes of administration for treating tissues, organs, limbs and even whole organisms with a therapeutically effective dose of compound (i.e., API) to protect such from the detrimental effects of injury. Where medical attention is not readily available, administration of the compounds of the invention provides time for the patient until they can receive other medical attention.

The compounds of the invention are also useful for inducing tissue regeneration and wound healing by preventing and/or delaying biological processes to promote wound healing and tissue regeneration. Where there is a substantial wound to the limb or organism, treating the biological matter with the compounds of the invention aid in the wound healing and tissue regeneration process by managing the biological processes that inhibit healing and regeneration. Other methods of using the compounds of the invention includes preventing or treating trauma such as cardiac arrest or stroke, and hemorrhagic shock. The risk of trauma from emergency surgical procedures, such as thoracotomy, laparotomy, and splenic transaction or cardiac surgery, aneurysm, surgery, brain surgery and the like are also treatable using the compounds of the invention.

Other methods of using the compounds of the invention include enhancing survivability and preventing ischemic injury resulting from cardiac arrest or stroke and reducing ischemic injury in a patient suffering from or at risk of cardiac arrest or stroke. A therapeutically effective dose of the compounds of the invention are administered to the patient before, after, or both before and after myocardial infarction, cardiac arrest or stroke.

Other methods include pretreating the patient's biological material prior to an ischemic or hypoxic injury or disease insult. Such methods are used when an injury or disease, with the potential to cause ischemia or hypoxia, is scheduled or elected in advance, or predicted in advance to likely occur, such as major surgery where blood loss may occur spontaneously or as a result of a procedure. Other anticipated procedures include cardiopulmonary bypass in which oxygenation of the blood may be compromised or vascular delivery of blood may be reduced (as in the setting of coronary artery bypass graft (CABG) surgery). Still other such procedures include treatment of organ donors prior to removal of donor organs for transport and transplantation into a recipient in need of an organ transplant. Other medical conditions include a risk of injury or disease progression is inherent, such as in the context of unstable angina, following angioplasty, bleeding aneurysms, hemorrhagic strokes, following major trauma or blood loss, or congestive heart failure. The risk may be capable of being diagnosed using a medical diagnostic test.

The compounds of the invention may also be used for enhancing survivability and preventing irreversible tissue damage from blood loss or other lack of oxygenation to cells or tissue, such as from lack of an adequate blood supply. Such tissue damage may result from actual blood loss or from conditions or diseases that cause blockage of blood flow to cells or tissue. Reduced blood pressure locally or overall in an organism may also occur, which reduces the amount of oxygen that is carried in the blood, and/or which reduces the number of oxygen carrying cells in the blood. Such conditions and/or diseases include blood clots and embolisms, cysts, growths, tumors, anemia, sickle cell anemia, hemophilia, other blood clotting diseases such as von Willebrand and ITP, atherosclerosis and the like. Such conditions and diseases also include those that create essentially hypoxic or anoxic conditions for cells or tissue in an organism because of an injury, disease, or condition.

The compounds of the invention may also be used to enhance the survivability of and prevent injury or damage to biological material undergoing hemorrhagic shock. The method includes treating the biological material at risk of or in a state of hemorrhagic shock with a therapeutically effective dose of the API within one hour of the injury or sooner. The patient may be transported to a controlled environment, such as surgery, where the initial cause of the injury can be addressed. The patient can then be brought back to normal function in a controlled manner. The first hour after injury, referred to as the golden hour, is critical to a successful outcome.

The compounds of the invention may also be used in the treatment of neurodegenerative diseases associated with ischemia, hypoxia, hypothermia, hyperproliferative disorders, immune disorders and the like. The biological condition may include one or more of neurological disease, cardiovascular disease, metabolic disease, infectious disease, lung disease, genetic disease, autoimmune disease, immune-related disease and the like.

The compounds of the invention may also be used to enhance the survivability of ex vivo biological matter (such as isolated cells, tissues and organs) subjected to hypoxic or ischemic conditions. Other such ex vivo biological material include platelets and other blood products as well as tissues and organs to be transplanted.

The compounds of the invention may also be used to enhance survivability of biological material in the laboratory or research context, such as where cell lines or laboratory organisms are purposefully subjected to hypoxic or ischemic conditions, such as during cryopreservation and storage. Cells, tissues or organs may also be stored or transported in the presence of the compounds of the invention.

The compounds of the invention may also be used to increase the survivability of donor tissues and organs extending the time before the donor tissue is transplanted into a recipient and blood flow is restored. Such methods may be combined with known preservation methods and materials, such as preservation agents and oxygen perfusion. Methods of using the compounds of the invention provide a way of enhancing survivability of platelets stored in an anoxic environment by treating the platelets with a therapeutically effective dose of the compounds of the invention during storage.

The compounds of the invention are also useful for preserving both non-living biological material and preserving or extending the shelf-life of non-biological material by treating the non-living biological matter or non-biological material with a therapeutically effective dose of the API.

The chemical name of a particular API compound is (R,R')-3,3'-trithiobis-2-acetamidopropanoic acid, bis-N-acetyl-cystine-trisulfide, or S,S'-di-N-acetyl-cysteine-sulfide, and it has the following free acid form structure:

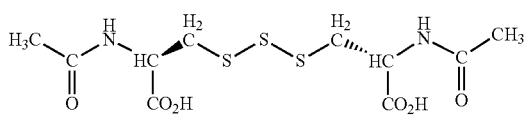

(I-a: Bis-N-acetly-cystine-trisulfide)

The chemical name of another particular API compound is (R,R')-3,3'-trithiobis-2-(methylsulfonylamido)propanoic acid or bis-N-methylsulfonyl-cystine-trisulfide and it has the following free acid form structure:

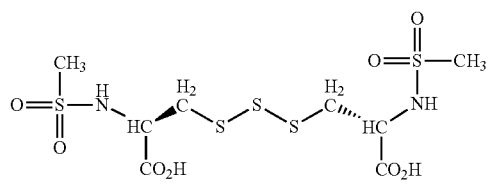

(I-d: N-methylsulfonyl-cystine-trisulfide)

In addition to the free acid form, these API compounds may also exist and be pharmaceutically active as a salt, ester, a hydrate, or a solvate. Their metabolites are also pharmacologically active. By means of illustration, bis-N-acetyl-cystine-trisulfide is a double-capped polysulfide whose capping moiety consists of N-acetyl-cysteine groups. These capping groups have the benefit of low toxicity to biological materials in their reduced sulfide state. N-acetyl-cysteine has an intravenous $LD_{50}$ in many mammals of approximately 300 mg/kg or greater. Specifically, N-acetyl-cysteine demonstrated an $LD_{50}$ IV in mouse of 3,800 mg/kg, an $LD_{50}$ IV in rat of 1,140 mg/kg; and an $LD_{50}$ IV in dog of 700 mg/kg.

The therapeutically effective dose of the API may be any amount in the range of 1 ppm, mg, mg/kg, or mg/m$^2$ to 1000 ppm, mg, mg/kg, or mg/m$^2$ or any range of amounts thereof. Alternatively, the dose or amount may be expressed as mM or M.

In various exemplary embodiments, a biological material is exposed to the compounds of the invention for any duration up to 30 seconds, 30 minutes, 1 hour, 1 day, 1 week, or any duration or range thereof.

Exemplary intravenous rates are in the range of 1 gtts/min or µgtts/min to 100 gtts/min or µgtts/min or any value or range thereof. The therapeutically effective dose may also be in terms of solution volume and API concentration, whereby the volume may be any value or range in the range of 1 ml to 1000 ml.

Methods of preparing parenteral dosage forms are set forth in Remington: The Science and Practice of Pharmacy, 21st Edition (Philadelphia College of Pharmacy and Science, 2005).

The therapeutically amount/dose of the API administered to biological material can be about, at least, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg, mg/kg, or mg/m2, or any range derivable therein.

Alternatively, the therapeutically effective amount/dose of the API may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 µM, mM or M, or any range derivable therein.

The biological material may be exposed to the instant parenteral dosage form containing the API and the parenteral carrier system for about, at least, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days or more, any range or combination therein, or in any suitable continuous or intermittent (or combinations thereof) dosing regimen.

Where administration is intravenous, the dosage form may be administered at a flow rate of about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 gtts/min or µgtts/min, or any range derivable therein.

The amount/duration of time may be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, or 1, 2, 3, 4, 5, 6, 7, 8, 9, 10, 11, 12 months, or any range derivable therein.

The amount of the parenteral solution may also be specified by volume (depending on the concentration of the API). The volumes may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mL or L, or any range therein, which may be administered as the total dosing regimen, in a single session, or, in a defined set of sessions.

EXAMPLES

Example 1

Preparation of Linear Symmetrical or Asymmetrical Trisulfides

The following reaction schemes illustrate methods of synthesizing the representative compounds of the present invention. It is understood that one skilled in the art may be able to make these compounds by similar methods or by combining other methods known to one skilled in the art. It is also understood that one skilled in the art would be able to make, in a similar manner as described below, other compounds of the present invention not specifically illustrated below by using the appropriate starting components and modifying the parameters of the synthesis as needed. In general, starting components may be obtained from commercial sources such as Aldrich Chemical Co. (Milwaukee, Wis., USA), etc. or synthesized according to sources known to those skilled in the art (see, e.g., Advanced Organic Chemistry: Reactions, Mechanisms, and Structure, 5$^{th}$ edition (Wiley, December 2000) or prepared as described in this invention.

Reaction Scheme 1 shown in FIGS. 10A, 10B, and 10C illustrates a synthetic approach to prepare both symmetrical and asymmetrical linear trisulfides, e.g., compounds of structure (I) wherein m is 3. The key intermediate, (R)-2-acetamido-3-((1,3-dioxoisoindolin-2-yl)disulfanyl)propanoic acid, was prepared by reacting of N-acetyl-L-cysteine with equal molar of 2,2'-thiodiisoindoline-1,3-dione in 80% $CH_3CN/H_2O$ at room temperature for 24 hours. This pure intermediate was obtained by chromatography on silica-gel, and characterized by $^1$H-NMR and LC-MS. Reaction of (R)-2-acetamido-3-((1,3-dioxoisoindolin-2-yl)disulfanyl)propanoic acid with the corresponding protected cysteine- or thio-containing analogs in 50% i-PrOH/$H_2O$ at room temperature gave its corresponding desired products. Final pure products, e.g., (R,R')-3,3'-trithiobis-2-acetamidopropanoic acid (I-a), were white solids and all of these pure products were obtained by preparative high-performance liquid chromatography (HPLC), and characterized by $^1$H-NMR, analytical HPLC, LC-MS and MS. The non-limiting examples disclosed in Reaction Scheme 1 have (M+H)$^+$ by positive APCI-MS: 357.00 (I-a); 414.10 (I-h); 371.10 (I-g); 385.07 (I-c); 393.06 (I-j).

Reaction Scheme 2 below further illustrates the preparation of the symmetrical compound (R,R')-3,3'-trithiobis-2-(methylsulfonylamido)propanoic acid (I-d). This synthetic scheme could be modified to prepare other symmetrical and asymmetrical compounds of structure (I). The key intermediate, (R)-2-methylsulfonylamido-3-((1,3-dioxoisoindolin-2-yl)disulfanyl)propanoic acid, was prepared by reacting N-methylsulfonyl-L-cysteine with equal molar of 2,2'-thiodiisoindoline-1,3-dione in 80% $CH_3CN/H_2O$ at room temperature for 24 hours. This pure intermediate was obtained by chromatography on silica-gel, and characterized by $^1$H-NMR and LC-MS. Reaction of (R)-2-methylsulfonyl-3-((1,3-dioxoisoindolin-2-yl)disulfanyl)propanoic acid with the corresponding protected cysteine- or thio-containing analogs in 50% i-PrOH/$H_2O$ at room temperature gave its corresponding desired products. The pure acid form of this compound (I-d), a white solid, was obtained by purification using preparative high-performance liquid chromatography (HPLC), and it was characterized by $^1$H-NMR, analytical HPLC, LC-MS and MS. It has 429.01 as (M+H)$^+$ by positive APCI-MS.

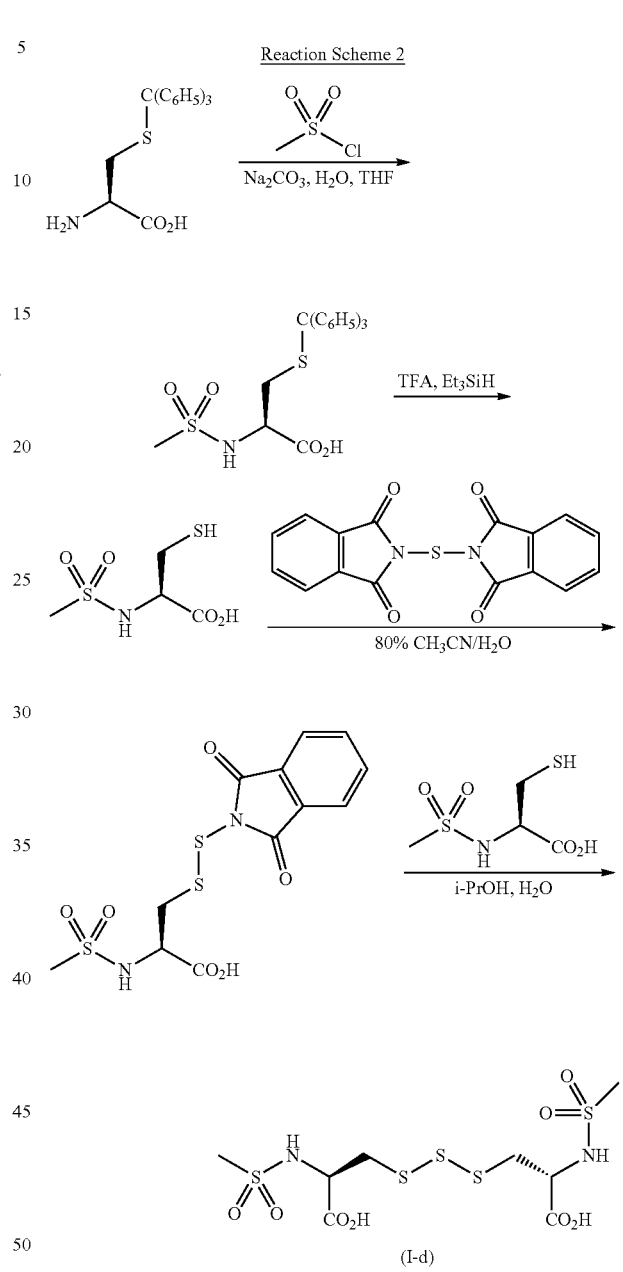

Reaction Scheme 2

As shown in Reaction Scheme 2 above, the N-methylsulfonyl-L-cysteine can be prepared by reacting the compound represented by the structure

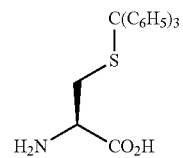

with methanesulfonyl chloride to produce a reaction product represented by the structure

27

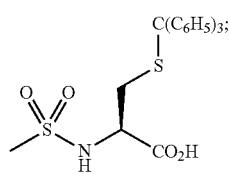

and treating the reaction product with triethylsilane and acid (such as trifluoroacetic acid) to produce N-methylsulfonyl-L-cysteine.

Reaction Scheme 2 illustrates preparation of a specific compound of the invention. However, as a general process for preparation of a variety of compounds according to the invention, the reaction can be illustrated as follows:

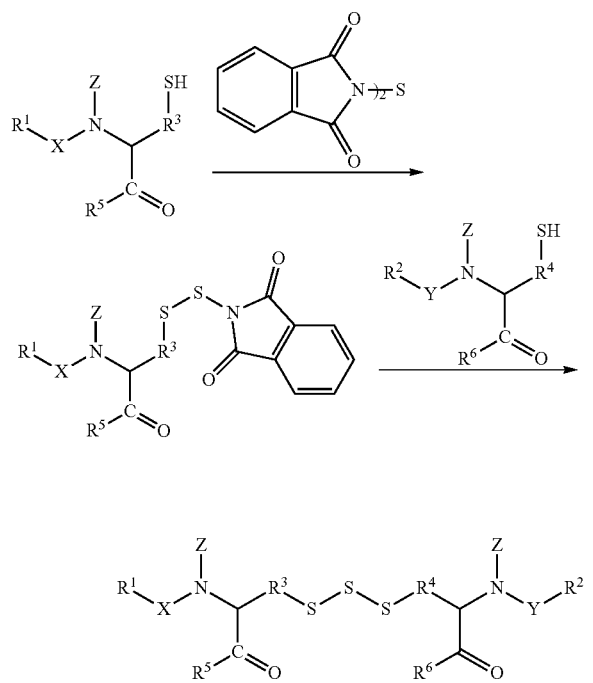

wherein $R^1$ and $R^2$ are independently a branched or straight chain $C_{1-10}$ alkyl; a branched or straight chain $C_{1-10}$ alkyl substituted with $-ONO_2$; or, a branched or straight chain $C_{1-10}$ alkyl substituted with $-OH$; wherein $R^3$ and $R^4$ are independently a branched or straight chain $C_{1-10}$ alkanediyl; wherein $R^5$ and $R^6$ are independently OH, an amino acid moiety, or, a straight or branched chain $C_{1-10}$ amine substituted with $-ONO_2$; wherein X and Y are independently C=O or $SO_2$; and, wherein Z is selected from H, $CH_3$, and $CH_2CH_3$. The ((1,3-dioxoisoindolin-2-yl)disulfanyl)-containing intermediate is prepared in acetonitrile and water, isolated, and reacted with the cysteine or thio-containing analog in 50% alcohol and water to produce the final product as described above.

(R,R')-3,3'-trithiobis-2-acetamidopropanoic acid, also named N,N'-diacetyl-L-cystine trisulfide or S,S'-di-N-acetyl-cysteine-Sulfide, can also be prepared as shown in Reaction Scheme 3 (WO9948865/U.S. Pat. No. 6,288,250): N,N'-thiodiphthalimide (11 mmol) was added to a solution of N-Acetyl-L-cysteine (23 mmol) in isopropanol. The reaction mixture was stirred at room temperature for 24 hours yielding a clear solution. After evaporation of isopropanol, the resulting white precipitate was removed by filtration. The filtrates were lyophilized to give the crude product. The pure trisulfide as a white solid was obtained by HPLC purification.

Reaction Scheme 3

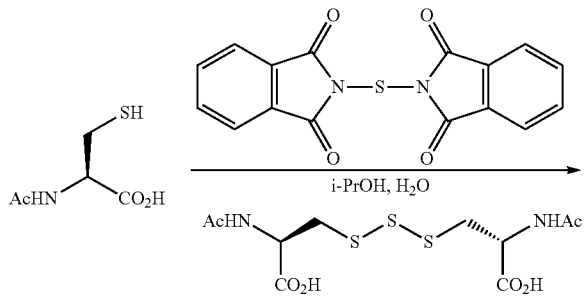

The compounds of the present invention may also be made by the following synthetic scheme disclosed in Mott A W et al. (Synthesis, (1984), (8), 657-60). A general synthetic scheme is shown in Reaction Scheme 4.

Reaction Scheme 4

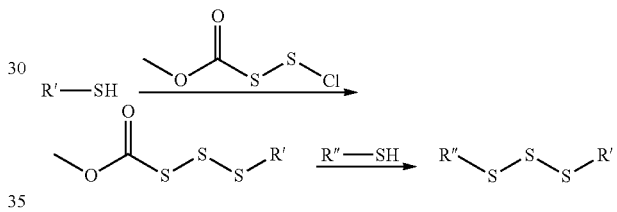

Suitable sulfur-transferring coupling agents may be used such as 2,2'-thiodiisoindoline-1,3-dione, N,N'-dibenzimidazyl sulfide, thiobis(imidazole), sulfur dichloride, sulfur monochloride, or elemental sulfur.

Example 2

Preparation of Cyclic Trisulfides

Compounds of structure (II) or (III) can be prepared by a modification of the procedure described by Lundin et al. (Tetrahedron Letters 1994, 35:6339-6342) to favor the intramolecular oxidation of the linear disulfide starting compound. For example, (5R,14S,17R)-17-acetamido-14-(carboxymethyl)-7,10,13,16-tetraoxo-1,2,3-trithia-6,9,12,15-tetraazacyclooctadecane-5-carboxylic acid was prepared as shown in Reaction Scheme 5: The starting material, Ac-Cys-Asp-Gly-Gly-Cys-OH, was prepared by FMOC-strategy on acid-labile resin supports using a commercially available peptide synthesizer, and was purified by reverse-phase HPLC using a $CH_3CN/H_2O$ (0.1% TFA) gradient. To a dilute solution (0.07 mM) of this linear peptide in 80% $CH_3CN/H_2O$ was added 1 eq. of 2,2'-thiodiisoindoline-1,3-dione, and this reaction mixture was stirred under argon at room temperature for 24 hours. The desired cyclic trisulfide was obtained by reverse-phase HPLC purification using a $CH_3CN/H_2O$ (0.1% TFA) gradient, and characterized by $^1$H-NMR, analytical HPLC, LC-MS and MS. It is a white powder which has 526.64 as $(M+H)^+$ by positive APCI-MS.

Reaction Scheme 5

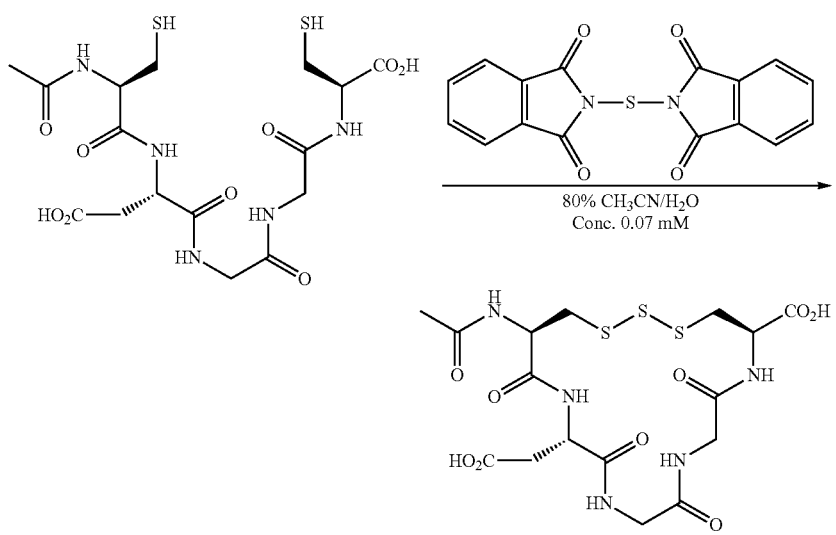

Example 3

Dosing Solution Preparation

Materials: Bis-N-acetyl-cystine-trisulfide cystine-trisulfide was stored at −20° C. Solution A was 1% citric acid in sterile water. Solution B was 0.5 N NaOH in saline (0.9% NaCl injection solution, Baxter).

Method: Vehicle solution was prepared by mixing 1 volume of solution B, 4 volumes of solution A, and 36 volumes of saline. The pH of the resulting vehicle solution is about 6. To prepare a bis-N-acetyl-cysteine-trisulfide dosing solution at a concentration of 30 mg/ml and about pH 6, the appropriate amount of bis-N-acetyl-cystine-trisulfide was weighed into a clear glass vial and cooled to −20° C. Solutions B and A were mixed at a 1:2 volume ratio, vortexed, and cooled to 4° C. on ice. 1 mL of the ice-cold solution was quickly added per 30 mg of bis-N-acetyl-cystine-trisulfide solid in the vial and vortexed immediately until the bis-N-acetyl-cystine-trisulfide solid was completely dissolved. The pH was adjusted with 0.5N NaOH as needed. The dosing solution was warmed to room temperature prior to parenteral administration. The dosing solution was stable for at least 1.5 hours at room temperature.

Bis-N-acetyl-cystine-trisulfide and Bis-N-methylsulfonamide-cystine-trisulfide exhibit unexpectedly high water solubility compared to other polysulfides (Tables 1 and 2). This allows formulation in aqueous solution at high concentration, which is important for preparing parenteral dosage forms.

TABLE 1

| Comparative Solubility Data | | | |
| --- | --- | --- | --- |
| Compound Structure | Water (mg/mL) | 20% PEG400 (mg/mL) | 17% HPBCD (mg/mL) |
| | 0.037 | 0.11 | >6 |
| | 0.22 | 0.31 | n.d. |
| | 0.10 | 0.24 | n.d. |

TABLE 1-continued

Comparative Solubility Data

| Compound Structure | Water (mg/mL) | 20% PEG400 (mg/mL) | 17% HPBCD (mg/mL) |
|---|---|---|---|
| Benzyl-S-S-S-S-CH2-CH(OH)-CH2-OH | 0.15 | 0.23 | 6.6 |
| HO2C-CH2CH2-S-S-S-CH2CH2-CO2H | poor | n.d | >20 (45% HPBCD) |
| AcNH-CH(COOH)-CH2-S-S-S-CH2CH2-phenyl | poor | n.d | 18 |
| H2N-CH(CO2H)-CH2-S-S-S-CH2-CH(NH2)-CO2H | Not soluble in water, 90% PEG400, 45% HPBCD, 45% Captisol, 2% Tween 80, 25% cremophor | | |
| AcNH-CH(CO2H)-CH2-S-S-S-CH2-CH(NHAc)-CO2H | >40 | n.d | n.d |
| MsNH-CH(CO2H)-CH2-S-S-S-CH2-CH(NHMs)-CO2H | >80 | n.d | n.d |

PEG, polyethylene glycol;
HPBCD, hydroxypropyl-beta-cyclodextrin,
n.d, no data.

TABLE 2

Comparative Vehicle Data

| Class | Compound Name | | Preferred Vehicle | MW |
|---|---|---|---|---|
| Allyl Polysulfide | Di allyl di-sulfide (H2C=CH-CH2-S-S-CH2-CH=CH2) | | 40% HPBCD/ 0.1% citric acid | 146.27 |
| Benzyl Polysulfide | Mono-benzyl-mono-2-hydroxyethyl-tetrasulfide (Ph-S-S-S-S-CH2CH2-OH) | | 40% HPBCD/ 0.1% citric acid | 264.45 |
| Cysteine-trisulfide | Bis-N-acetyl-cysteine-trisulfide | | aqueous | 356.44 |

Example 4

Increase of Biologically Available Sulfide in Blood and Plasma Thiosulfate by Intravenous Administration of Bis-N-acetyl cystine-trisulfide Pharmacokinetic experiments were conducted with groups of two to four animals consisting of 9-10 week old, male Sprague Dawley rats, 276-300 grams (Charles River Laboratories, Wilmington, Mass.) with a jugular vein catheter and a femoral vein catheter. Animals were allowed to acclimate in a temperature and humidity controlled environment for 1-3 days prior to the commencement of experimental procedures. Food and water were provided ad libitum.

A baseline blood sample (~0.4 mL) was collected from each rat through the jugular vein cannula into a heparin-coated syringe (1 mL volume) fitted with a 23 G Luer stub adapter. After sampling, the blood volume was replenished by slowly injecting 0.4 mL of a solution of 50 u/mL heparin in saline through the jugular vein cannula. A bolus dose of bis-N-acetyl-cystine-trisulfide (e.g., 16 or 32 mg/kg IV in dosing solution was injected through the femoral vein catheter. Both bis-N-acetyl-cystine-trisulfide dosing solution and vehicle had a pH of about 6.0 (5.8 to 6.2). Blood (~0.4 mL) was drawn at 0, 1, 5, 10, 30, 60 & 120 minutes after dosing from the jugular vein cannula using a heparin-coated syringe (1 mL) with a 23 G Luer stub adapter. Blood volume was replenished as described above. Biologically available sulfide in blood and plasma thiosulfate were measured as described (Wintner et al. 2010, Br. J. Pharmacology 160:941-957).

Figure 1:
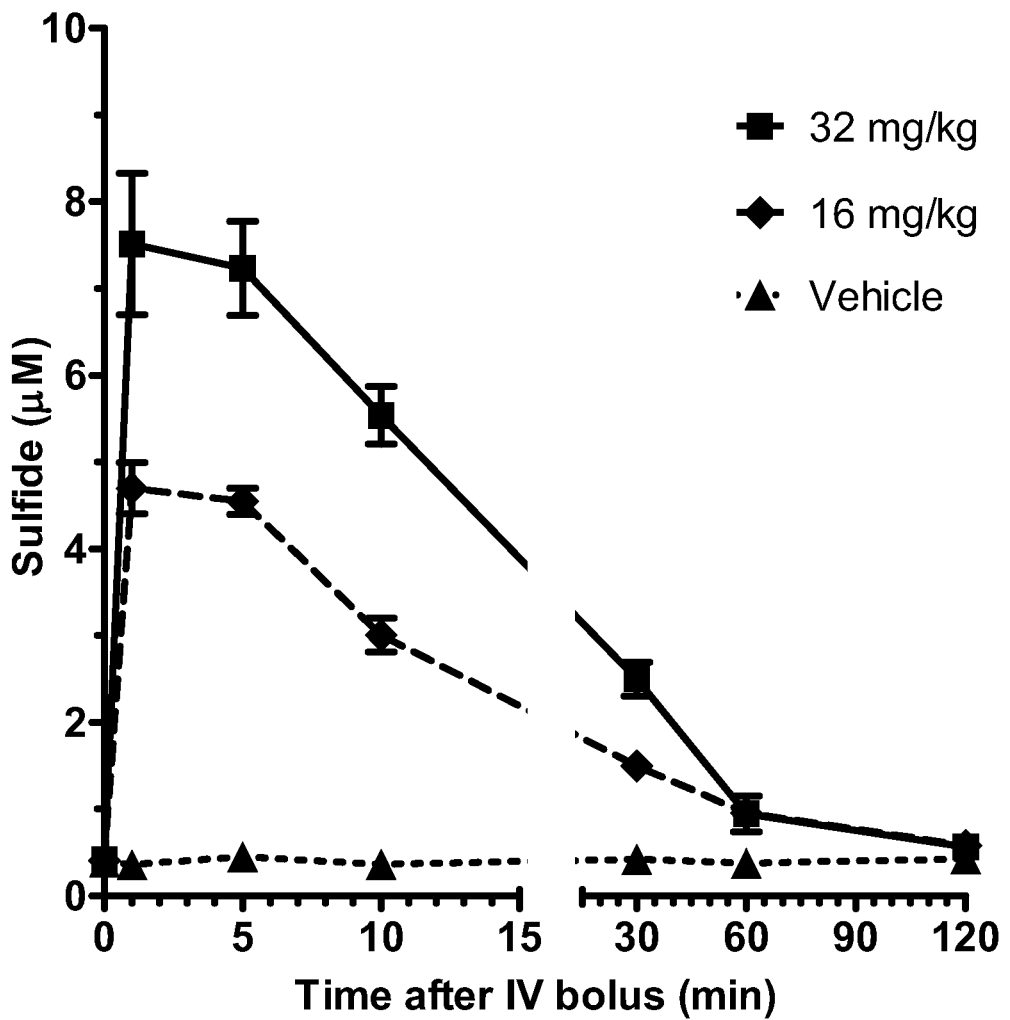
Figure 2:
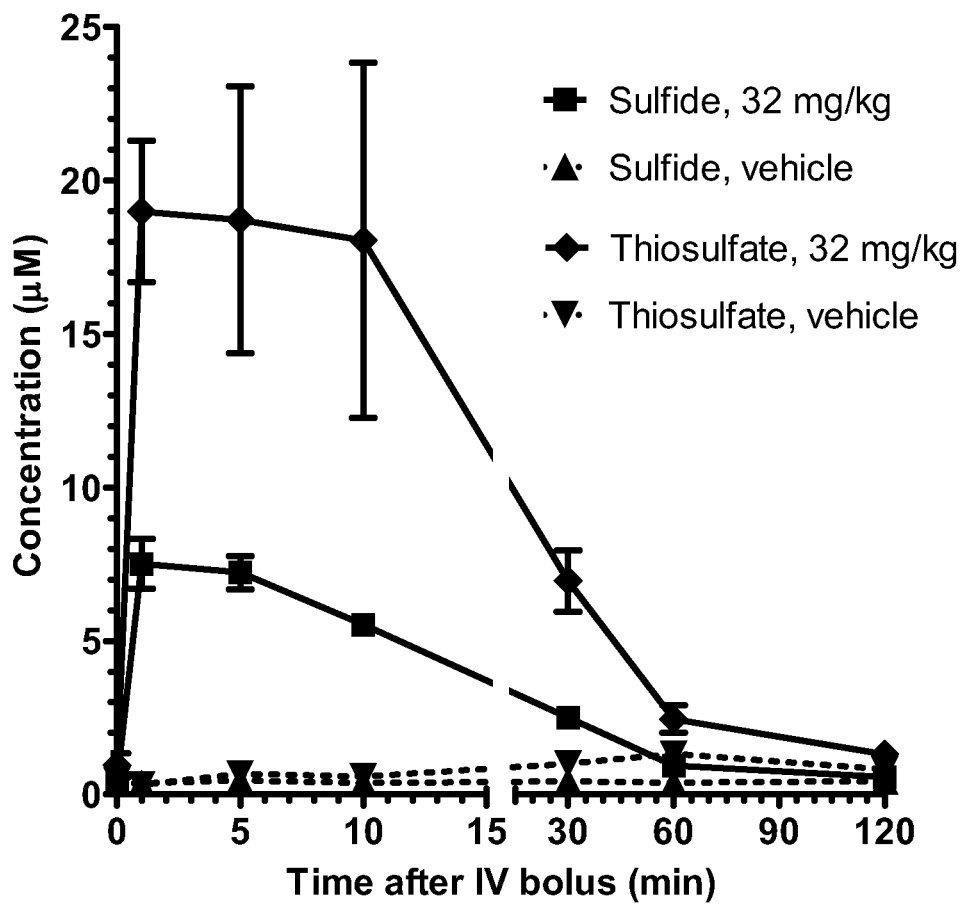
Figure 6:
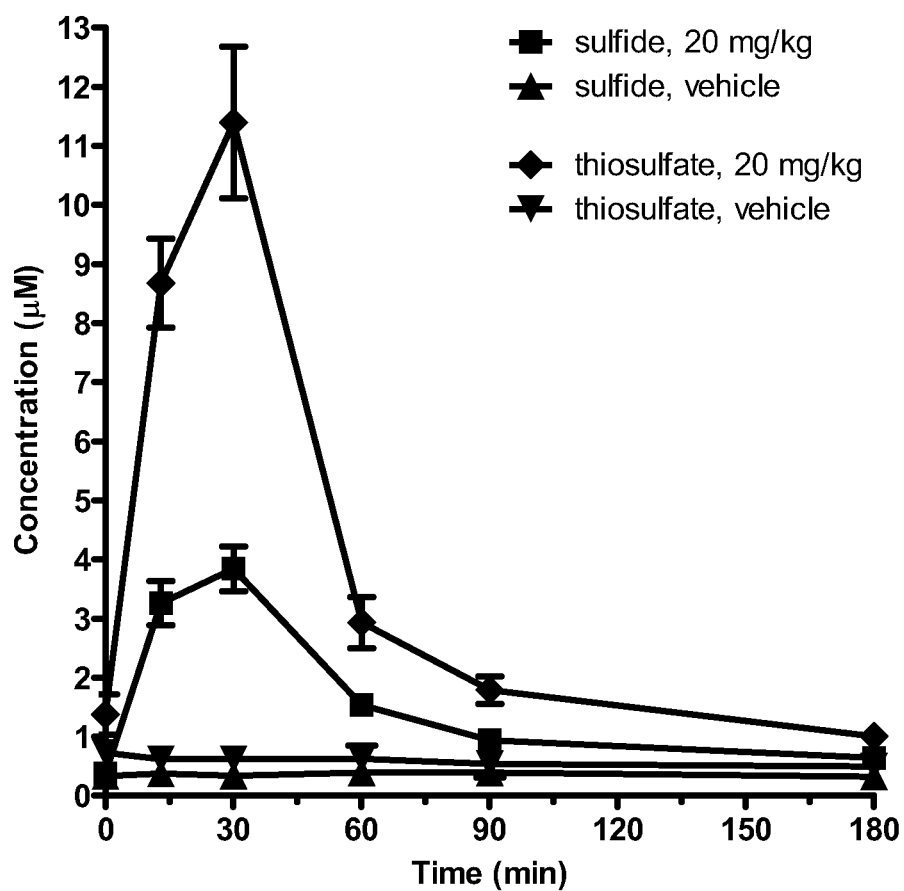

Intravenous administration of 16 or 32 mg/kg bis-N-acetyl-cystine-trisulfide leads to a dose-dependent elevation of biologically available sulfide in blood as well as an elevation of plasma thiosulfate indicating that the compound delivers metabolizable sulfide to blood (see FIGS. 1 and 2). Elevation of blood sulfide can be extended by administration of repeated intravenous boli of bis-N-acetyl-cystine-trisulfide as demonstrated in FIG. 6. Biologically available sulfide and plasma thiosulfate persists for 3 hours after two consecutive IV bolus injections of 20 mg/kg bis-N-acetyl-cystine-trisulfide at t=0 and t=15 min.

Example 5

No Elevation of Free Sulfide by Intravenous Administration of Bis-N-acetyl-cystine-trisulfide Male CD rats (350-450 g, Charles River Laboratories) were anesthetized by IV pentobarbital injection and the right jugular vein carefully exposed and dissected away from the surrounding tissue. An amperometric hydrogen sulfide sensor (World Precision Instruments, Sarasota, Fla., Cat. #ISO-H2S-2) was inserted into the jugular and advanced into the vena cava. Sensor current was monitored using a Powerlab 8/30 (ADInstruments, Colorado Springs, Colo.). Once a stable baseline current was attained, the animals received either vehicle (pH matched saline) or bis-N-acetyl-cystine-trisulfide (20 mg/kg) administered over 1 min via a left femoral vein catheter, and sensor current was monitored over 30 min. Changes in current were calibrated against an IK-1001 standard curve generated with the sensor in deoxygenated 50 mM HEPES, 150 mM NaCl, 1 mM DTPA at 37° C. and pH 7.4.

Figure 3:
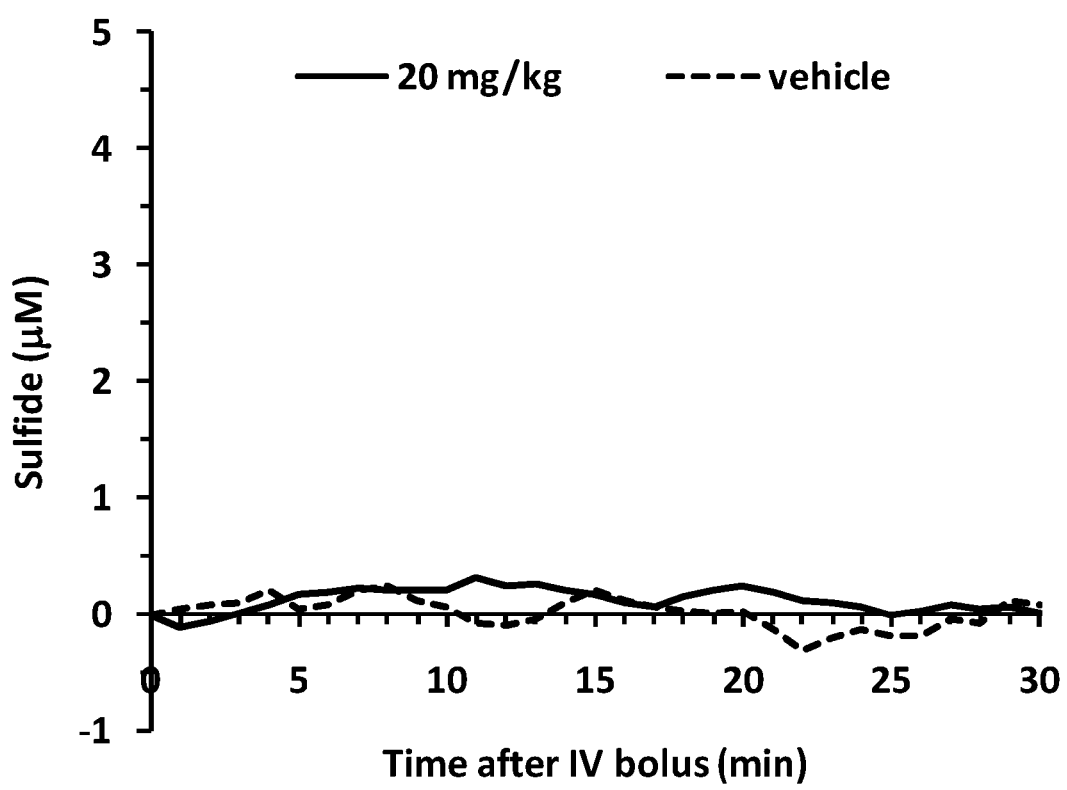

Intravenous injection of 20 mg/kg bis-N-acetyl-cystine-trisulfide does not lead to any measurable increase of free sulfide in blood, similar to the injection of vehicle (FIG. 3). This result differs from the robust elevation of free sulfide observed after intravenous injection of a 1 mg/kg sodium sulfide solution (Wintner et al. 2010, Br J Pharmacology 160:941-957). Taken together with the data for mono-bromo-bimane reactive sulfide, this experiment demonstrates that bis-N-acetyl-cystine-trisulfide delivers biologically available sulfide to blood in a chemical form different from free sulfide.

The absence of free sulfide is reflected in the low toxicity of the sulfide-releasing compounds. The maximum tolerated dose in mice for intravenous injections of bis-N-acetyl-cystine-trisulfide was found to be approximately 500 mg/kg, consistent with the absence of free sulfide in blood.

Example 6

Figure 4A:
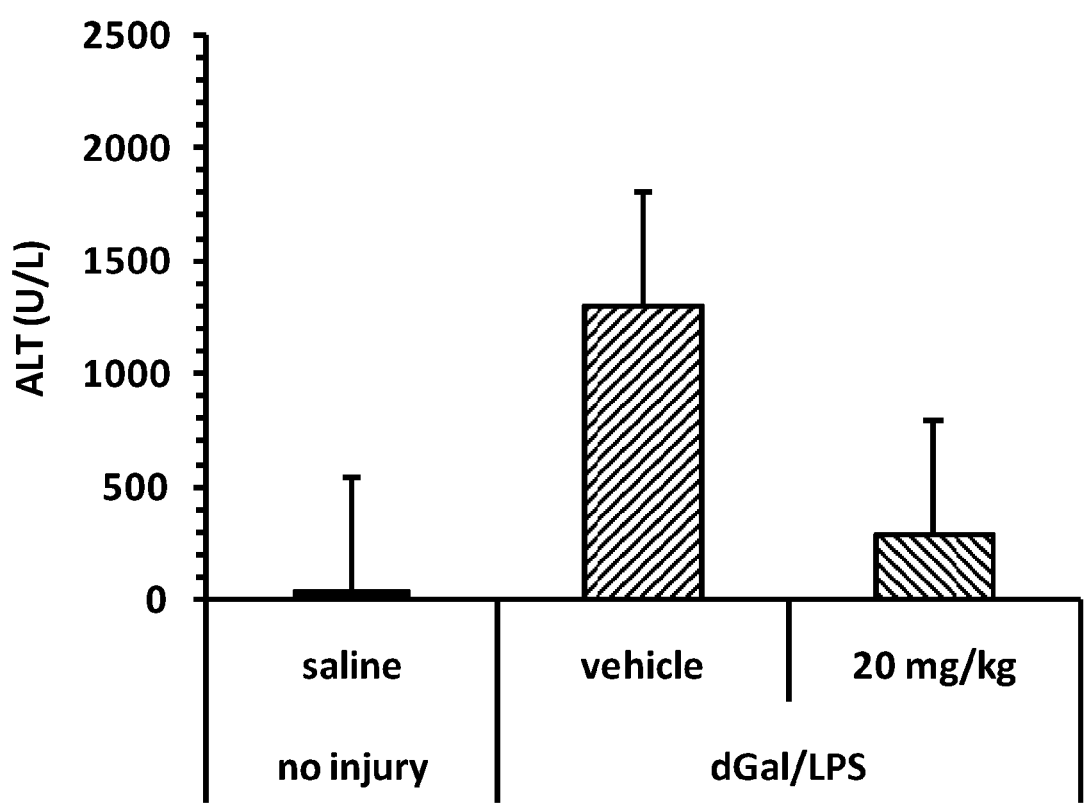
Figure 4B:
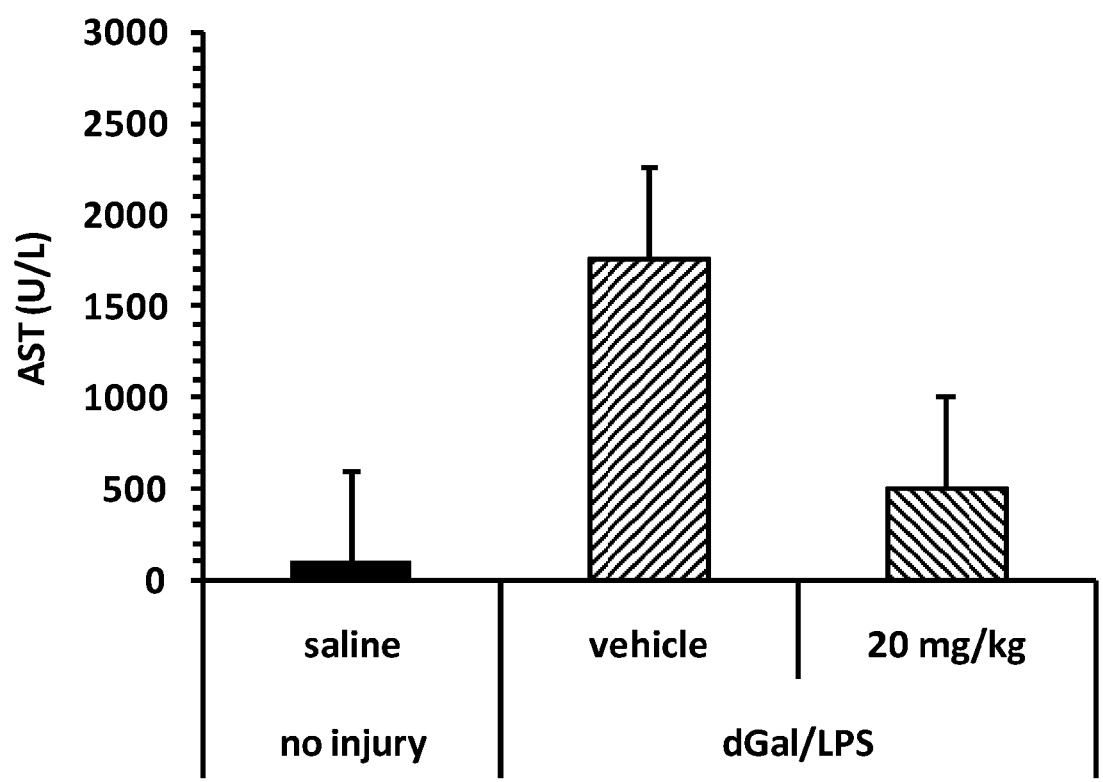
Figure 5:
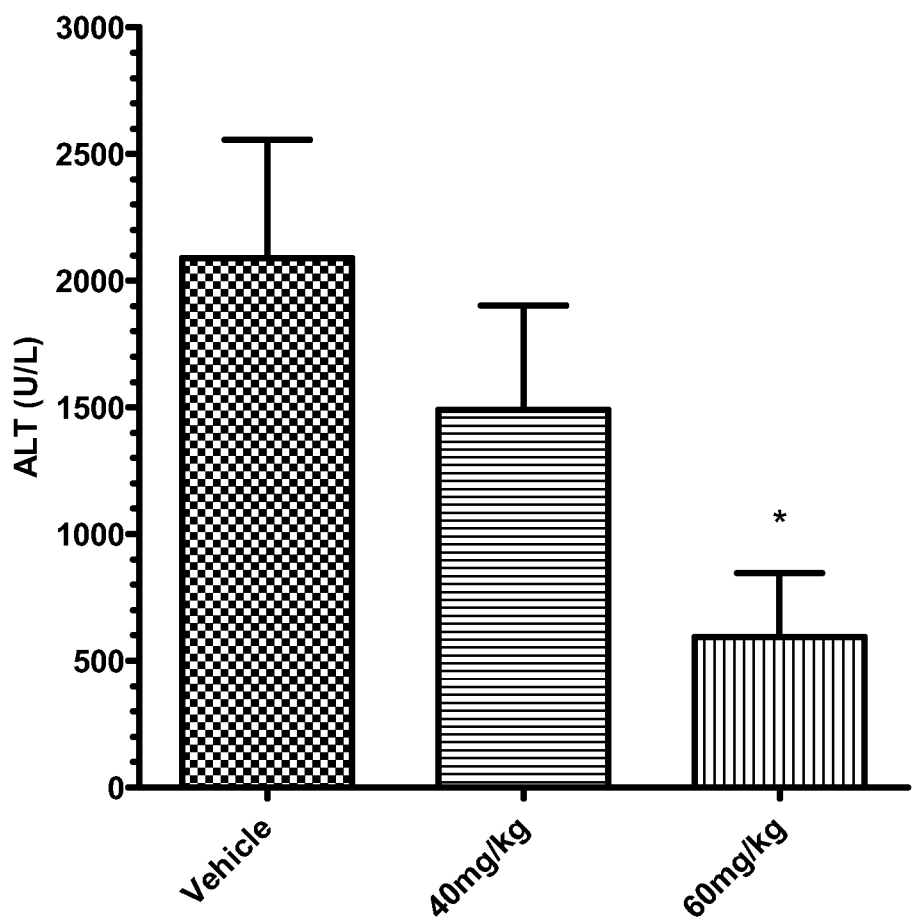

Protection from Endotoxin-Induced Liver Damage by Bis-N-acetyl-cysteine-trisulfide Male C57BL/6 mice, (22 to 24 g, Charles River Laboratories) were acclimated in a temperature and humidity controlled environment for 1-3 days prior to commencement of the experimental procedures. All cages were placed on water heating pads set at 30° C. Liver injury was caused by injecting mice intraperitoneally with 800 mg/kg d-Galactosamine (dGal), followed 30 min later by 100 µg/kg lipopolysaccharide (LPS) (FIG. 4) or with 1000 mg/kg dGal, followed 30 min later by 120 µg/kg LPS (FIG. 5). Bis-N-acetyl-cystine-trisulfide at 20 mg/kg (FIG. 4) or 40 and 60 mg/kg (FIG. 5), or vehicle were injected intraperitoneally 30 min later. Blood was collected by cardiac puncture under isoflurane anesthesia five hours after LPS injection. Serum was prepared and markers of liver injury, alanine aminotransferase (ALT) and aspartate aminotransferase (AST) measured. Bis-N-acetyl-cysteine trisulfide protected from endotoxin-induced liver injury (FIGS. 4 and 5).

Example 7

Figure 7:
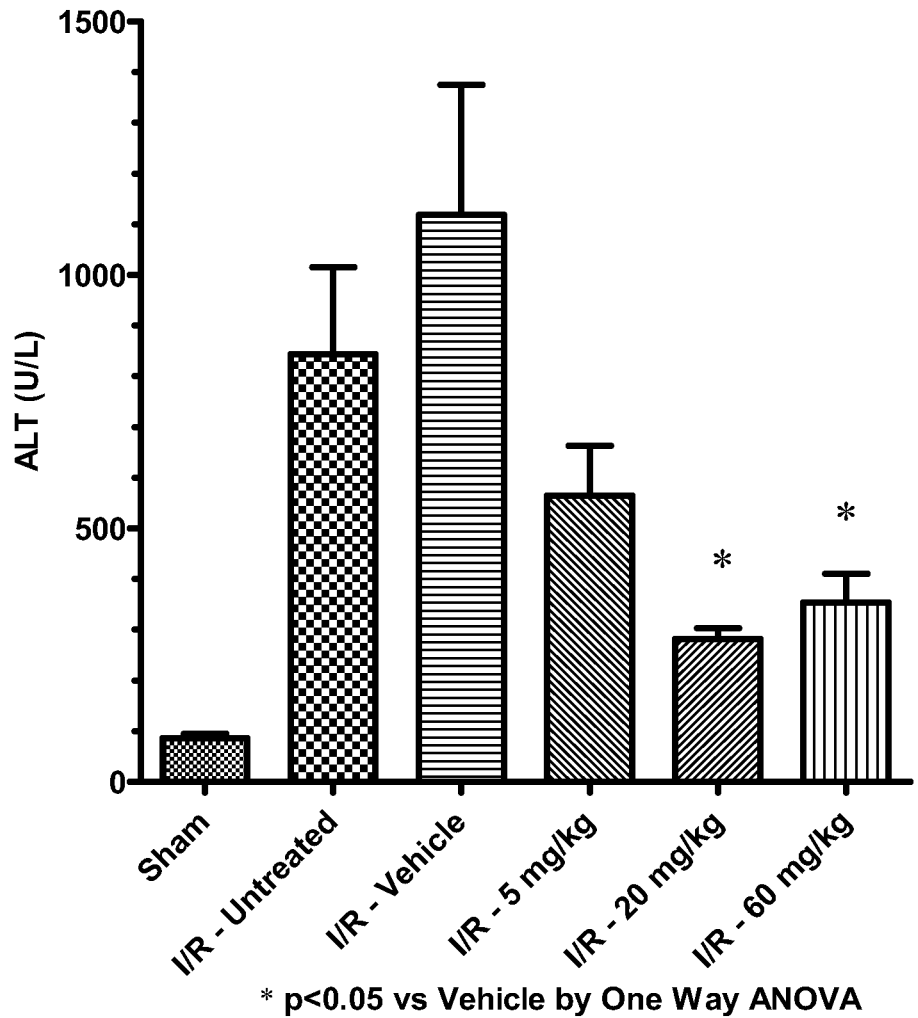
FIG. 7 is a graph demonstrating the protection of the livers of mice from ischemia/reperfusion (I/R) injury by an intravenous bolus of bis-N-acetyl-cystine-trisulfide at 5, 20 or 60 mg/kg, compared to untreated and vehicle-treated conditions. Hepatic injury was determined by measuring plasma ALT.
Figure 8:
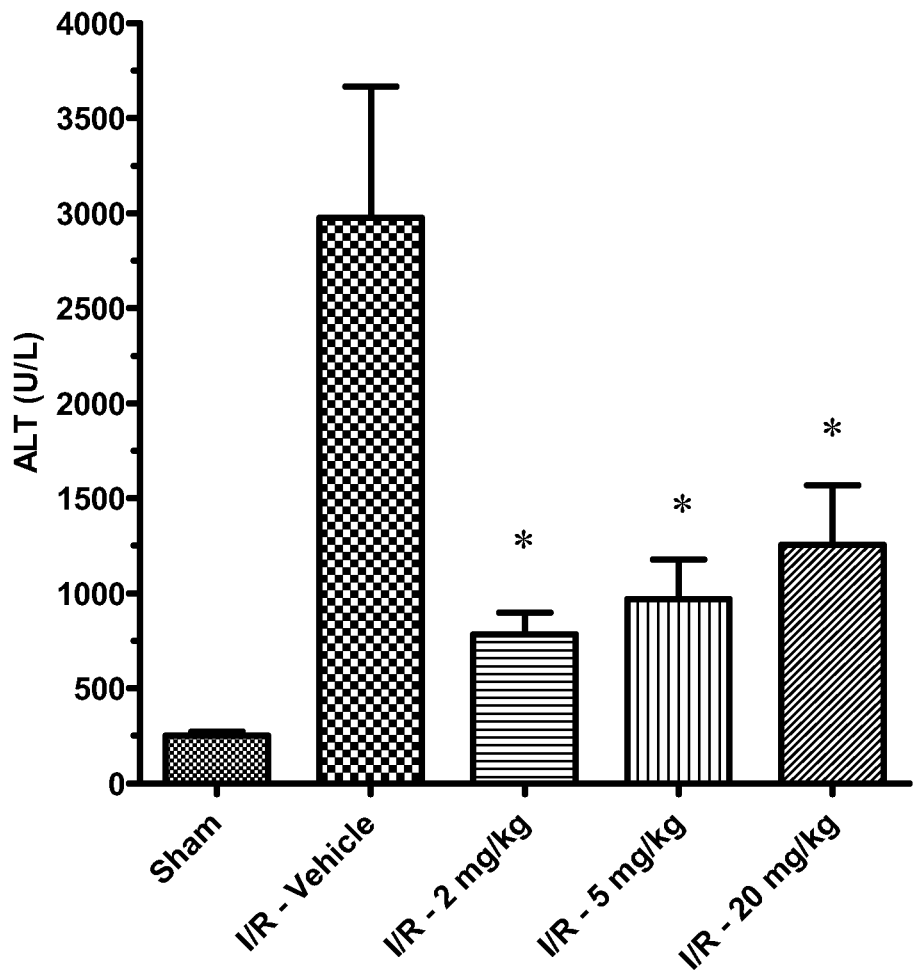
FIG. 8 is a graph demonstrating the protection of the livers of mice from ischemia/reperfusion (I/R) injury by an intravenous bolus of bis-N-methylsulfonamide-cystine-trisulfide at 2, 5, or 20 mg/kg, compared to untreated and vehicle-treated conditions. Hepatic injury was determined by measuring plasma ALT.

Protection from Ischemia/Reperfusion-Induced Liver Damage by Trisulfide Test Compounds C57BL/6 mice were anesthetized with a ketamine/xylazine combination given via intraperitoneal injection. A midline laparotomy was performed to expose the viscera and the stomach and intestines were moved laterally to allow for unimpeded visualization of the liver. A micoaneurysm clip was applied to the hepatic artery and portal vein to create a partial liver ischemia encompassing the medial and left lateral lobes (approximately 70% of the liver). In the last 5 minutes of a 45 minute occlusion, vehicle or a test compound (5, 20, or 60 mg/kg bis-N-acetyl-cystine-trisulfide; or 2, 5, or mg/kg bis-N-methylsulfonyl-cystine-trisulfide) was injected into the inferior vena cava. The aneurysm clips were removed at 45 minutes to restore hepatic blood flow which was confirmed visually. The abdominal incision was closed using wound clips and animals were recovered in a warmed chamber with 100% oxygen. Five hours after reperfusion, blood was collected by cardiac puncture to measure serum alanine aminotransferase (ALT). Intravenous boli of 5 to 60 mg/kg bis-N-acetyl-cystine-trisulfide and of 2 to 20 mg/kg bis-N-methylsulfonyl-cystine-trisulfide protected the liver from ischemia/reperfusion injury (FIGS. 7 and 8).

Example 8

Generation of Biologically Available Sulfide in Blood by Bis-N-acetyl-cystine-trisulfide and Inhibition of Formation by N-Aminoethyl-maleimide The chemical nature of biologically available sulfide in blood was probed with the thiol-reactive reagent N-aminoethyl-maleimide (NAEM) which binds to free thiols and perthiols on proteins and blocks them from participating further in thiol-mediated chemical reactions. Biologically available sulfide was generated in blood by adding 1.3 mM bis-N-acetyl-cystine-trisulfide to 2 mL of whole rat blood. Biologically available sulfide was measured by derivatization with mono-bromo-bimane and levels of bis-N-acetyl-cystine-trisulfide in blood were followed by LC/MS/MS. Bis-N-acetyl-cystine-trisulfide was consumed within 5 minutes while generating biologically available sulfide (FIG. 9). Pretreatment of rat blood with 20 mM NAEM for 30 min prior to addition of bis-N-acetyl-cystine-trisulfide reduced consumption of bis-N-acetyl-cystine-trisulfide and almost completely blocked the production of biologically available sulfide. The concentration of NAEM was chosen such that all of it was consumed within 1 min of preincubation with rat blood (FIG. 9), thus avoiding any potential interference with biologically-available sulfide production by bis-N-acetyl-cystine-trisulfide in blood. The experiment demonstrates that biologically available sulfide created by exposure to sulfide donor reagents such as N-acetyl-cystine-trisulfide resides on thiols and perthiols in blood that can be blocked with NAEM.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of making a linear symmetrical or asymmetrical trisulfide compound represented by the structure:

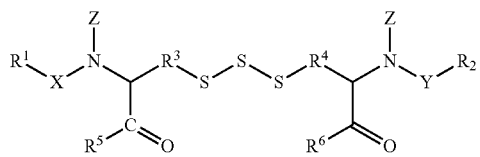

wherein $R^1$ and $R^2$ are independently a branched or straight chain $C_{1-10}$ alkyl; a branched or straight chain $C_{1-10}$ alkyl substituted with —$ONO_2$; or, a branched or straight chain $C_{1-10}$ alkyl substituted with —OH; wherein $R^3$ and $R^4$ are independently a branched or straight chain $C_{1-10}$ alkanediyl; wherein $R^5$ and $R^6$ are independently OH, an amino acid moiety, or, a straight or branched chain $C_{1-10}$ amine substituted with —$ONO_2$; wherein X and Y are independently C=O or $SO_2$; and, wherein Z is selected from H, $CH_3$, and $CH_2CH_3$; the method comprising:

reacting a compound represented by the following structure

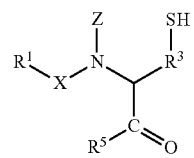

wherein $R^1$, X, $R^3$ and $R^5$ are as defined above, with an equal molar amount of 2,2'-thiodiisoindoline-1,3-dione in acetonitrile and water to produce a ((1,3-dioxoisoindolin-2-yl)disulfanyl)-containing intermediate;

isolating the intermediate; and reacting the intermediate with a compound represented by the following structure

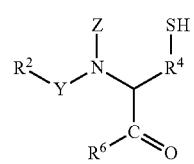

wherein $R^2$, X, $R^4$ and $R^6$ are as defined above, in an aqueous alcohol solution, thereby forming the trisulfide compound.

2. The method of claim 1, wherein the aqueous alcohol solution comprises 50% isopropanol.

3. The method of claim 1 wherein the method comprises reacting a compound represented by the structure:

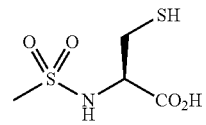

with the 2,2'-thiodiisoindoline-1,3-dione, thereby forming the trisulfide compound represented by the structure

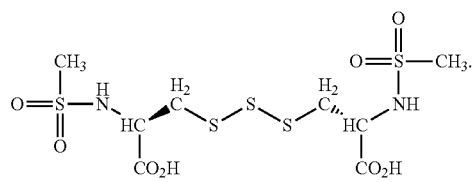 [SMILES: CS(=O)(=O)N[C@@H](CSSSC[C@H](NS(C)(=O)=O)C(=O)O)C(=O)O]

4. The method of claim 1 wherein the compound which is reacted with the 2,2'-thiodiisoindoline-1,3-dione is prepared by a method comprising reacting a compound represented by the structure

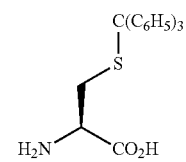

with methanesulfonyl chloride to produce a reaction product represented by the structure

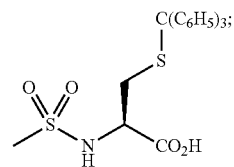

and treating the reaction product with triethylsilane and trifluoroacetic acid to produce the compound.

5. A method of treating or prophylactically treating to prevent injury to biological matter exposed to ischemic or hypoxic conditions comprising administering to a patient in need thereof a therapeutically effective dose of a compound selected from the group consisting of

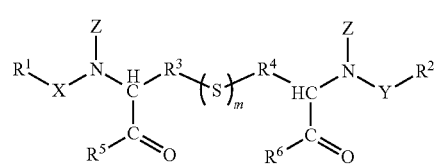

wherein $R^1$ and $R^2$ are independently a branched or straight chain $C_{1-10}$ alkyl; a branched or straight chain $C_{1-10}$ alkyl substituted with —ONO$_2$; or, a branched or straight chain C$_{1-10}$ alkyl substituted with —OH; wherein R$^3$ and R$^4$ are independently a branched or straight chain C$_{1-10}$ alkanediyl; wherein R$^5$ and R$^6$ are independently OH, an amino acid moiety, or, a straight or branched chain C$_{1-10}$ amine substituted with —ONO$_2$; wherein X and Y are independently C=O or SO$_2$; and, wherein m is 3 or 4; Z is selected from H, CH$_3$, and CH$_2$CH$_3$; or a salt, ester, hydrate, solvate or stereoisomer thereof.

6. The method of claim 5 wherein the hypoxic or ischemic conditions are related to reperfusion injury, tissue or organ transplantation, septic shock, cardiac arrest, exposure to cold or radiation, burns, wounds, amputations, stroke, hemorrhagic shock, surgical procedures, systemic inflammatory response syndrome, acute respiratory distress syndrome, kidney failure, liver failure or multiple organ failure.

7. The method of claim 5 wherein the compound is administered parenterally, intravenously, as a bolus or a repeated bolus.

8. The method of claim 6 wherein the hypoxic or ischemic conditions are related to reperfusion injury, tissue or organ transplantation, cardiac arrest, stroke, or hemorrhagic shock.

* * * * *